United States Patent [19]

Berg et al.

[11] Patent Number: 5,300,565
[45] Date of Patent: Apr. 5, 1994

[54] PARTICULATE, ABSORBENT, POLYMERIC COMPOSITIONS CONTAINING INTERPARTICLE CROSSLINKED AGGREGATES

[75] Inventors: Charles J. Berg; Frank H. Lahrman; Donald C. Roe, all of Cincinnati, Ohio

[73] Assignee: The Procter & Gamble Company, Cincinnati, Ohio

[21] Appl. No.: 503,506

[22] Filed: Apr. 2, 1990

[51] Int. Cl.$^5$ ............................................. C08G 63/48
[52] U.S. Cl. .............................. 525/54.2; 525/54.24; 525/54.26; 525/54.31
[58] Field of Search ............... 525/54.2, 54.24, 54.26, 525/54.31

[56] References Cited

U.S. PATENT DOCUMENTS

| | | | |
|---|---|---|---|
| 3,900,378 | 8/1975 | Yen et al. | 204/159.14 |
| 4,076,663 | 2/1978 | Masuda et al. | 260/17.4 GC |
| 4,117,184 | 9/1978 | Erickson et al. | 428/224 |
| 4,172,066 | 10/1979 | Zweigle et al. | 128/284 |
| 4,394,930 | 7/1983 | Korpman | 220/444 |
| 4,415,388 | 11/1983 | Korpman | 156/78 |
| 4,654,039 | 3/1987 | Brandt et al. | 604/358 |
| 4,699,619 | 10/1987 | Bernardin | 604/358 |
| 4,734,788 | 3/1988 | Emmett et al. | 358/300 |
| 4,755,560 | 7/1988 | Ito et al. | 525/100 |
| 4,834,735 | 5/1989 | Alemany et al. | 604/368 |
| 4,904,249 | 2/1990 | Miller et al. | 604/378 |
| 4,916,328 | 4/1990 | Culp, III | 307/39 |
| 5,047,023 | 9/1991 | Berg | 604/368 |
| 5,068,127 | 11/1991 | Fournes et al. | 427/237 |
| 5,102,597 | 4/1992 | Roe et al. | 264/126 |
| 5,124,188 | 6/1992 | Roe et al. | 428/72 |
| 5,140,076 | 8/1992 | Hatsuda et al. | 525/375 |
| 5,149,334 | 9/1992 | Lahrman et al. | 604/367 |
| 5,149,335 | 9/1992 | Kellenberger et al. | 604/372 |
| 5,171,781 | 12/1992 | Farrar | 524/547 |
| 5,180,622 | 1/1993 | Berg et al. | 428/283 |

FOREIGN PATENT DOCUMENTS

| | | |
|---|---|---|
| 0317106A2 | 5/1989 | European Pat. Off. |
| 0349241 | 1/1990 | European Pat. Off. |
| 0401044 | 6/1990 | European Pat. Off. |
| 0443627A2 | 8/1991 | European Pat. Off. |
| WO90/08789 | 8/1990 | PCT Int'l Appl. |
| WO91/15368 | 10/1991 | PCT Int'l Appl. |
| 0522570A1 | 1/1993 | PCT Int'l Appl. |
| 94861 | 1/1988 | Taiwan |
| 2140471 | 11/1984 | United Kingdom |
| 2162525 | 2/1986 | United Kingdom |

*Primary Examiner*—James J. Bell
*Attorney, Agent, or Firm*—Steven W. Miller; Loretta J. Henderson; Bart S. Hersko

[57] ABSTRACT

Particulate, absorbent, polymeric compositions comprising interparticle crosslinked aggregates. The interparticle crosslinked aggregates comprise precursor particles of substantially water-insoluble, absorbent, hydrogel-forming, polymer material; and an interparticle crosslinking agent reacted with the polymer material of the precursor particles to form crosslink bonds between the precursor particles. Sufficient interparticle crosslinked aggregates are formed when the mass average particle size of the resultant polymeric composition has been increased by at least about 25% over the mass average particle size of the precursor particles. The resultant polymeric composition provides improved structural integrity, an increased acquisition rate, and minimal gel blocking properties.

29 Claims, 12 Drawing Sheets

PARTICULATE, ABSORBENT, POLYMERIC COMPOSITIONS CONTAINING INTERPARTICLE CROSSLINKED AGGREGATES

FIELD OF THE INVENTION

The present invention relates to improved particulate, absorbent, polymeric compositions. Such polymeric compositions are those which, upon contacting fluids (i.e., liquids) such as water or body exudates, swell and imbibe such fluids. These polymeric compositions are especially useful by themselves or in absorbent members such as fibrous web structures which can be incorporated into absorbent articles such as diapers, adult incontinence pads, sanitary napkins, and the like. The present invention also relates to methods for producing such polymeric compositions.

BACKGROUND OF THE INVENTION

Particulate, absorbent, polymeric compositions are capable of absorbing large quantities of fluids such as water and body exudates and which are further capable of retaining such absorbed fluids under moderate pressures. These absorption characteristics of such polymeric compositions make them especially useful for incorporation into absorbent articles such as diapers. For example, U.S. Pat. No. 3,699,103 issued to Harper et al. on Jun. 13, 1972 and U.S. Pat. No. 3,670,731 issued to Harmon on Jun. 20, 1972, both disclose the use of particulate, absorbent, polymeric compositions (also referred to as hydrogel, hydrocolloid, or superabsorbent materials) in absorbent articles.

Conventional particulate, absorbent, polymeric compositions, however, have the limitation that their rate of fluid uptake is much lower than that of conventional cellulosic fiber webs due to the small surface area to mass ratio of the constituent particles of the polymeric composition. The surface area to mass ratio of the particles of the particulate, absorbent, polymeric composition is important since it can control the overall fluid uptake rate of the bulk polymeric composition. The surface area to mass ratio, and hence the fluid uptake rate, can be substantially increased by decreasing the mass average particle size of the particles in the bulk polymeric composition. However, when these small particles or fines swell upon contact with liquids, the particles, when incorporated in a fiber web, tend to be easily forced into the interfiber capillaries of the web. The swollen or partially swollen fines may also form a mass of coagulated gel held together by fluid surface tension forces, thus forming a gel barrier. In either case, resistance to fluid flow through the structure is increased as fluid flow channels are blocked within the fiber web or the gel mass resulting in a marked decrease in permeability. These phenomena are commonly referred to as "gel blocking."

One attempt to break this trade-off between the rate of fluid uptake and gel blocking has been to agglomerate, via water, a multiplicity of small particles to larger "nuclei" particles. Such water-agglomerating techniques are disclosed in Japanese Patent Laid-Open SHO 61(1986)-97,333 and Japanese Patent Laid-Open SHO 61(1986)-101,586. While water-agglomeration of the particles does result in a modest increase in the fluid uptake rate due to an increased surface area to mass ratio of the larger particles, the water-agglomerated particles dissociate upon contact and/or swelling with an aqueous solution. This results in a concentration of swollen or partially swollen free fine particles that will contribute to an increased gel blocking effect via the mechanisms described above.

Another attempted solution to the problem has been to surface treat the discrete particles. One specific surface treatment method is to surface crosslink the discrete particles so that each individual particle has a higher crosslink density among the polymer chains at or near the surface of the particles. Such surface crosslinking techniques are described in U.S. Pat. No. 4,666,983 issued to Tsubakimoto et al. on May 19, 1987; and U.S. Pat. No. 4,734,478 issued to Tsubakimoto et al. on Mar. 29, 1988. Surface crosslinking of the particles results in a modest reduction in one form of the above-defined gel blocking by reducing the tendency of the discrete particles to coagulate into an impermeable gel mass during swelling. However, the rate of fluid uptake of the particles is not increased because the surface area to mass ratio of the particles remains relatively constant.

Therefore, the present invention seeks to resolve the above problems by providing improved particulate, absorbent, polymeric compositions having a high rate of fluid uptake with minimal gel blocking properties.

Thus, it is an object of the present invention to provide particulate, absorbent, polymeric compositions with a high rate of fluid uptake.

It is a further object of the present invention to provide particulate, absorbent, polymeric compositions that display minimal gel blocking properties.

It is a still further object of the present invention to provide particulate, absorbent, polymeric compositions that have a high resistance to compression during use (i.e., during swelling) in order to maintain and/or increase the permeability of absorbent products incorporating such polymeric compositions.

It is an even further object of the present invention to provide particulate, absorbent, polymeric compositions having minimal dissociation of fine particles upon fluid contact or swelling.

It is an even still further object of the present invention to provide particulate, absorbent, polymeric compositions having minimal free fines in the dry state.

It is an even further object of the present invention to provide particulate, absorbent, polymeric compositions that achieve predefined rates of fluid uptake by selecting specific characteristics of the precursor particles such as the mass average particle size or absorptive capacity.

It is another object of the present invention to provide a method for producing such particulate, absorbent, polymeric compositions.

It is a further object of the present invention to provide improved absorbent products, absorbent members, and absorbent articles (such as diapers or sanitary napkins) incorporating the particulate, absorbent, polymeric compositions of the present invention.

SUMMARY OF THE INVENTION

The present invention provides improved particulate, absorbent, polymeric compositions comprising interparticle crosslinked aggregates. The interparticle crosslinked aggregates comprise precursor particles of substantially water-insoluble, absorbent, hydrogel-forming, polymer material; and an interparticle crosslinking agent reacted with the polymer material of the precursor particles to form crosslink bonds between the precursor particles. When the mass average particle size of the resultant polymeric composition has been increased by at least about 25% over the mass average particle size of the precursor particles, a sufficient number of interparticle crosslinked aggregates are formed so that the resultant polymeric composition has improved properties. The interparticle crosslinked aggregates have improved structural integrity (i.e., the aggregate remains intact when swollen and has a relatively high compressive resistance), an increased acquisition rate, and minimal gel blocking properties.

When contacted with a liquid, the interparticle crosslinked aggregates will swell generally isotropically (i.e., swell equally in all dimensions), even under moderate confining pressures, and absorb such liquids. The isotropic swelling of the interparticle crosslinked aggregates is achieved since the interparticle crosslinked aggregates maintain the structural and spatial relationships of the precursor particles even when swollen (i.e., the aggregates maintain their integrity in both the dry and the swollen states). Thus, the precursor particles forming the interparticle crosslinked aggregates will not dissociate upon contact with or swelling in liquids (such that the interparticle crosslinked aggregates are "fluid stable") so that gel blocking is minimized. Further, the interparticle crosslinked aggregates have relatively high rates of fluid uptake to provide rapidly acquiring polymeric compositions due to the high surface area to mass ratio of the interparticle crosslinked aggregates. Thus, the interparticle crosslinked aggregates of the present invention provide a polymeric composition capable of rapidly absorbing liquids while minimizing gel blocking properties.

The present invention also relates to improved particulate, absorbent, polymeric compositions comprising interparticle crosslinked aggregates formed from precursor particles having a relatively small particle size (i.e., fine precursor particles). By using fine precursor particles to form the interparticle crosslinked aggregates, the surface area to mass ratio of the aggregates is increased over the surface area to mass ratio of precursor particles having the same particle size as the aggregate such that the resultant polymeric compositions incorporating such interparticle crosslinked aggregates have particularly high rates of fluid uptake (Swelling Rate) while minimizing their gel blocking properties by removing free fines from the swollen or partially swollen polymeric composition. These interparticle crosslinked aggregates also provide an efficient way to reduce fines in the dry bulk polymeric composition that improves the handling and performance characteristics of such polymeric compositions.

The present invention further relates to absorbent products, absorbent members, and absorbent articles incorporating the polymeric compositions of the present invention comprising interparticle crosslinked aggregates. The performance of such products are enhanced by providing such polymeric compositions having high rates of fluid uptake with minimal gel blocking properties. Further, the larger size of the interparticle crosslinked aggregates assists in opening capillary channels of fibrous webs incorporating such polymeric compositions. Further, the interparticle crosslinked aggregates minimize migration of swollen or dry particles through the absorbent structures due to their structural integrity (i.e., finer particles remain bonded together).

The present invention further relates to methods of producing such polymeric compositions comprising interparticle crosslinked aggregates. In the method of the present invention, an interparticle crosslinking agent is applied onto the precursor particles; the precursor particles are physically associated to form a multiplicity of aggregates; and the interparticle crosslinking agent is reacted with the polymer material of the precursor particles of the aggregates, while maintaining the physical association of the precursor particles, to form crosslink bonds between the precursor particles to form interparticle crosslinked aggregates. The interparticle crosslinked aggregates are formed to such an extent that the mass average particle size of the polymeric composition is at least about 25% greater than average particle size of the mass precursor particles. In a preferred method, the interparticle crosslinked aggregates are also surface crosslinked.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

Particulate, absorbent, polymeric compositions of the present invention are materials capable of absorbing large quantities of fluids (i.e., liquids) such as water and/or body exudates (e.g., urine or menses) and which are capable of retaining such fluids under moderate pressures. Typically, the particulate, absorbent, polymeric compositions of the present invention will swell and rapidly absorb the fluids with little or no incidence of gel blocking.

Figure 12:
FIG. 12 is a photomicrograph enlarged approximately 30 times of a particulate, absorbent, polymeric composition of the present invention made in accordance with Example 6 herein.
Figure 14:
FIG. 14 is a photomicrograph enlarged approximately 40 times of a particulate, absorbent, polymeric composition of the present invention made in accordance with Example 1 herein, wherein the mass median particle size of the precursor particles is equal to about 84 microns.

As shown in FIGS. 12 and 14, the polymeric compositions of the present invention are in a particulate form. The term "particulate" is used herein to mean that the elements comprising the polymeric composition are in the form of discrete units denominated "particles". The particles can comprise granules, pulverulents, spheres, flakes, fibers, aggregates or agglomerates. Thus, the particles can have any desired shape such as cubic; rod-like; polyhedral; spherical; rounded; angular; irregular; randomly-sized irregular shapes (e.g., pulverulent products of a grinding or pulverizing step or aggregates) or shapes having a large greatest dimension/smallest dimension ratio like needle-like, flake-like, or fibrous shapes, and the like. As shown in FIGS. 12 and 14, the particles preferably comprise randomly-sized irregular shaped interparticle crosslinked aggregates.

The polymeric compositions of the present invention are referred to herein as comprising "particles". It should be noted, however, that the term particles include aggregates. As used herein, the term "aggregate" is used to mean a single "particle" formed from two or more previously independent particles (i.e., "precursor particles") joined together. While it is relatively easy for those of ordinary skill in the art to determine which particles of the polymeric composition are aggregates, a specific procedure for identifying such aggregates is hereinafter defined in the Test Methods section. Thus, throughout the specification, the term "particle" is used herein to mean the resultant units making up the polymeric composition, including aggregates, while the term "precursor particles" refers to the initial units used in forming the resultant particles of the polymeric composition, especially the aggregates. Particles that are formed from a single precursor particle will be specifically referred to as nonaggregate particles.

Although the particles and the precursor particles may have sizes varying over a wide range, specific particle size distributions and sizes are preferred. For purposes of the present invention, particle size is defined as the dimension of a particle or precursor particle which is determined by sieve size analysis. Thus, for example, a particle that is retained on a standard #30 sieve with 600 micron openings is considered to have a particle size greater than 600 microns, a particle that passes through the #30 sieve with 600 micron openings and is retained on a standard #35 sieve with 500 micron openings is considered to have a particle size between 500 and 600 microns, and a particle that passes through the #35 sieve with 500 micron openings is considered to have a particle size less than 500 microns. In preferred embodiments of the present invention, the particles will generally range in size from about 1 micron to about 2000 microns in diameter or cross-section, more preferably, the particles will have a particle size from about 20 microns to about 1000 microns.

Further, for purposes of this invention, the mass average particle size of the particles or the precursor particles is important in determining the characteristics and properties of the polymeric composition. The mass average particle size of a given sample of particles or precursor particles is defined as the particle size which is the average particle size of the sample on a mass basis. A method for determining the mass average particle size of a sample is described hereinafter in the Test Methods section. In preferred embodiments of the present invention, the mass average particle size of the particles is from about 100 microns to about 1500 microns, more preferably from about 200 microns to about 1000 microns.

The polymeric compositions of the present invention are formed from polymer materials capable of absorbing large quantities of liquids. (Such polymer materials are commonly referred to as hydrogel, hydrocolloid, or superabsorbent materials.) The polymeric compositions preferably comprise particles of substantially water-insoluble, absorbent, hydrogel-forming, polymer material. The polymer materials useful for the particles of the polymeric compositions may widely vary. The specific polymer materials useful in the present invention will be discussed herein with respect to the polymer materials forming the precursor particles.

Figure 13:
FIG. 13 is a photomicrograph enlarged approximately 60 times of an interparticle crosslinked aggregate of the present invention selected from the sample shown in FIG. 12.
Figure 15:
FIG. 15 is a photomicrograph enlarged approximately 110 times of an interparticle crosslinked aggregate of the present invention selected from the sample shown in FIG. 14.

The particulate, absorbent, polymeric compositions of the present invention comprise interparticle crosslinked aggregates. Interparticle crosslinked aggregates are the aggregate particles formed by joining together two or more previously independent precursor particles. The precursor particles are joined together by interparticle crosslinking agents applied thereto and subjected to conditions, while maintaining the physical association of the precursor particles, which are sufficient to react the interparticle crosslinking agent with the polymer material of the precursor particles to form crosslink bonds between the precursor particles that form the aggregate. FIGS. 13 and 15 show photomicrographs of interparticle crosslinked aggregates of the present invention.

Precursor particles form the interparticle crosslinked aggregates of the present invention. The precursor particles comprise substantially water-insoluble, absorbent, hydrogel-forming, polymer material. Examples of polymer materials suitable for use as the precursor particles herein (and thus the particles of the resultant polymeric composition) include those which are prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Some non-acid monomers may also be used to prepare the precursor particles herein. Such non-acid monomers can include, for example, the water-soluble or water-dispersible esters of the acid-containing monomers as well as monomers which contain no carboxyl or sulfonic acid groups at all. Optional non-acid monomers can thus include monomers containing the following types of functional groups: carboxylic acid or sulfonic acid esters, hydroxyl groups, amide-groups, amino groups, nitrile groups and quaternary ammonium salt groups. These non-acid monomers are well known materials and are described in greater detail, for example, in U.S. Pat. No. 4,076,663 issued to Masuda et al. on Feb. 28, 1978 and in U.S. Pat. No. 4,062,817 issued to Westerman on Dec. 13, 1977, both of which are incorporated herein by reference.

Olefinically unsaturated carboxylic acid and carboxylic acid anhydride monomers include the acrylic acids typified by acrylic acid itself, methacrylic acid, ethacrylic acid, alpha-chloroacrylic acid, alpha-cyano acrylic acid, beta-methyl acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-steryl acrylic acid, itaconic acid, citraconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyltoluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

Preferred polymer materials for use in the present invention possess a carboxyl group. These polymers include hydrolyzed starch-acrylonitrile graft copolymer, partially neutralized starch-acrylonitrile graft copolymer, starch-acrylic acid graft copolymer, partially neutralized starch-acrylic acid graft copolymer, saponified vinyl acetate-acrylic ester copolymers, hydrolyzed acrylonitrile or acrylamide copolymers, slightly network crosslinked products of any of the foregoing copolymers, partially neutralized polyacrylic acid, and slightly network crosslinked products of partially neutralized polyacrylic acid. These polymers may be used either independently or in the form of a mixture of two or more monomers, compounds, or the like. Examples of these polymer materials are disclosed in U.S. Pat. No. 3,661,875; U.S. Pat. No. 4,076,663; U.S. Pat. No. 4,093,776; U.S. Pat. No. 4,666,983; and U.S. Pat. No. 4,734,498.

Most preferred polymer materials for use as the precursor particles are slightly network crosslinked products of partially neutralized polyacrylic acids and starch derivatives therefrom. Most preferably, the particles comprise from about 50 to about 95%, preferably about 75%, neutralized, slightly network crosslinked, polyacrylic acid (e.g., poly (sodium acrylate/acrylic acid)).

As described above, the precursor particles preferably are polymer materials that are slightly network crosslinked. Network crosslinking serves to render the precursor particles substantially water-insoluble and in part serves to determine the absorptive capacity and extractable polymer content characteristics of the precursor particles and the resultant polymeric composition. Processes for network crosslinking the polymers and typical network crosslinking agents are described in greater detail in the hereinbefore-referenced U.S. Pat. No. 4,076,663.

The individual precursor particles may be formed in any conventional manner. Typical and preferred processes for producing the individual precursor particles are described in: U.S. Pat. No. Re. 32,649 entitled "Hydrogel-Forming Polymer Compositions For Use In Absorbent Structures" reissued to Kerryn A. Brandt, Steven A. Goldman, and Thomas A. Inglin on Apr. 19, 1988; U.S. Pat. No. 4,666,983 entitled "Absorbent Article" issued to Tsuneo Tsubakimoto, Tadao Shimomura, and Yoshio Irie on May 19, 1987; and U.S. Pat. No. 4,625,001 entitled "Method For Continuous Production Of Cross-Linked Polymer" issued to Tsuneo Tsubakimoto, Tadao Shimomura, and Yoshio Irie on Nov. 25, 1986. These patents are incorporated herein by reference.

Preferred methods for forming the precursor particles are those that involve aqueous solution or other solution polymerization methods. As described in the above-referenced U.S. Pat. No. Re. 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. The mass of polymer material thereby formed is then pulverized or chopped to form the individual precursor particles useful in forming the interparticle crosslinked aggregates and the polymeric compositions herein.

More specifically, the aqueous solution polymerization method for producing the individual precursor particles comprises the preparation of an aqueous reaction mixture in which to carry out polymerization to form the desired precursor particles. One element of such a reaction mixture is the acid group-containing monomer material which will form the "backbone" of the precursor particles to be produced. The reaction mixture will generally comprise about 100 parts by weight of the monomer material. Another component of the aqueous reaction mixture comprises a network crosslinking agent. Network crosslinking agents useful in forming the precursor particles are described in more detail in the above-referenced U.S. Pat. No. Re. 32,649 issued to Brandt et al.; U.S. Pat. No. 4,666,983 issued to Tsubakimoto et al.; and U.S. Pat. No. 4,625,001 issued to Tsubakimoto et al. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer material). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomer materials including esters of the essential unsaturated acidic functional group-containing monomers or other co-monomers containing no carboxyl or sulfonic acid functionalities at all.

The aqueous reaction mixture is subjected to polymerization conditions which are sufficient to produce in the mixture substantially water-insoluble, absorbent, hydrogel-forming, polymer materials. The polymerization conditions are also discussed in more detail in the three above-referenced patents. Such polymerization conditions generally involve heating (thermal activation techniques) to a polymerization temperature from about 0° C. to about 100° C., more preferably from about 5° C. to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the polymer materials formed in the aqueous reaction mixture are also preferably neutralized. Neutralization can be carried out in any conventional manner which results in at least about 25 mole percent, and more preferably at least about 50 mole percent, of the total monomer utilized to form the polymer material being acid group-containing monomers that are neutralized with a salt-forming cation. Such salt-forming cations include, for example, alkali metals, ammonium, substituted ammonium and amines as discussed in further detail in the above-referenced U.S. Pat. No. Re. 32,649 issued to Brandt et al.

While it is preferred that the precursor particles be manufactured using an aqueous solution polymerization process, it is also possible to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. The resultant precursor particles are generally spherical in shape. Inverse suspension polymerization procedures are described in greater detail in U.S. Pat. No. 4,340,706 issued to Obaysashi et al. on Jul. 20, 1982; U.S. Pat. No. 4,506,052 issued to Flesher et al. on Mar. 19, 1985; and U.S. Pat. No. 4,735,987 issued to Morita et al. on Apr. 5, 1988; each of these patents being incorporated herein by reference.

In preferred embodiments of the present invention, the precursor particles used to form the interparticle crosslinked aggregates are substantially dry. The term "substantially dry" is used herein to mean that the precursor particles have a liquid content, typically water or other solution content, less than about 50%, preferably less than about 20%, more preferably less than about 10%, by weight of the precursor particles. Typically, the liquid content of the precursor particles is in the range of from about 0.01% to about 5% by weight of the precursor particles. The individual precursor particles can be dried by any conventional method such as by heating. Alternatively, when the precursor particles are formed using an aqueous reaction mixture, water can be removed from the reaction mixture by azeotropic distillation. The polymer-containing aqueous reaction mixture can also be treated with a dewatering solvent such as methanol. Combinations of these drying procedures may also be used. The dewatered mass of polymer material can then be chopped or pulverized to form substantially dry precursor particles of substantially water-insoluble, absorbent, hydrogel-forming, polymer material.

Preferred precursor particles of the present invention are those which exhibit a high absorptive capacity so that the resultant polymeric composition formed from such precursor particles also has a high absorptive capacity. Absorptive capacity refers to the capacity of a given polymer material to absorb liquids with which it comes into contact. Absorptive capacity can vary significantly with the nature of the liquid being absorbed and with the manner in which the liquid contacts the polymer material. For purposes of this invention, Absorptive Capacity is defined in terms of the amount of Synthetic Urine (as hereinafter defined) absorbed by any given polymer material in terms of grams of Synthetic Urine per gram of polymer material in a procedure hereinafter defined in the Test Methods section. Preferred precursor particles of the present invention are those which have an Absorptive Capacity of at least about 20 grams, more preferably at least about 25 grams, of Synthetic Urine per gram of polymer material. Typically, the polymer materials herein have an Absorptive Capacity of from about 40 to about 70 grams in Synthetic Urine per gram of polymer material. Precursor particles having this relatively high Absorptive Capacity characteristic are especially useful in absorbent members and absorbent articles since the resultant interparticle crosslinked aggregates formed from such precursor particles can, by definition, hold desirably high amounts of discharged body exudates such as urine.

The individual precursor particles may optionally be surface treated. For example, U.S. Pat. No. 4,824,901 issued to Alexander et al. on Apr. 25, 1989, discloses the surface treatment of polymeric particles with a polyquaternary amine. If surface treated, the precursor particles are preferably surface crosslinked as disclosed in U.S. Pat. No. 4,666,983, entitled "Absorbent Article", issued to Tsubakimoto et al. on May 19, 1987; and U.S. Pat. No. 4,734,478, entitled "Water Absorbing Agent" issued to Tsubakimoto et al. on Mar. 29, 1988; which patents are incorporated herein by reference. As disclosed in the Tsubakimoto et al. '983 patent, the individual precursor particles may be surface crosslinked by applying a surface crosslinking agent onto the precursor particles and reacting the surface crosslinking agent with the polymer material on the surface of the particles.

While all of the precursor particles of a given interparticle crosslinked aggregate or of the resultant polymeric composition are preferably formed of the same polymer material with the same properties, this need not be the case. For example, some precursor particles may comprise a polymer material of a starch-acrylic acid graft copolymer while other precursor particles may comprise a polymer material of slightly network crosslinked products of partially neutralized polyacrylic acid. Further, the precursor particles of a specific interparticle crosslinked aggregate or in the resultant polymeric composition may vary in shape, absorptive capacity, or any other property or characteristic of the precursor particles. In a preferred embodiment of the present invention, the precursor particles comprise a polymer material consisting essentially of slightly network crosslinked products of partially neutralized polyacrylic acid; each precursor particle having similar properties.

The precursor particles can comprise granules, pulverulents, spheres, flakes, fibers, aggregates, agglomerates, or the like. Thus, the precursor particles can have any desired shape such as cubic; rod-like; polyhedral; spherical; rounded; angular; irregular; randomly-sized irregular shapes (i.e., pulverulent products of a grinding or pulverizing step) or shapes such as needle-like, flake-like, or fibrous shapes. Preferably, as shown in FIGS. 12-15, the precursor particles are in a finely divided powder form of randomly-sized irregular shaped pulverulent granules or flakes.

The precursor particles may also have a size varying over a wide range. Preferably, the precursor particles will have a size in the range of from about 1 micron to about 2000 microns in diameter or cross-section. More preferably, the precursor particles will have a particle size in the range of from about 20 microns to about 1000 microns. The mass average particle size of the precursor particles will generally be from about 20 microns to about 1500 microns, more preferably from about 50 microns to about 1000 microns. In preferred embodiments of the present invention, the precursor particles preferably have a mass average particle size less than about 1000 microns, more preferably less than about 600 microns, most preferably less than about 500 microns.

The interparticle crosslinked aggregates of the present invention also comprise an interparticle crosslinking agent. The interparticle crosslinking agent is applied onto the precursor particles and reacted with the polymer material of the precursor particles while physical association between the precursor particles is maintained. This reaction forms crosslink bonds between the precursor particles. Thus, the crosslink bonds are interparticle in nature (i.e., between different precursor particles). Without wishing to be bound by theory or limit the present invention, it is believed the reaction of the interparticle crosslinking agent with the polymer material of the precursor particles forms crosslink bonds between the polymer chains of different precursor particles (i.e., interparticle crosslink bonds). For the preferred polymers herein, it is believed the interparticle crosslinking agent reacts to form crosslink bonds between the carboxyl groups of the precursor particles. Without wishing to be bound by theory or limit the scope of the invention, for the preferred polymer materials possessing carboxyl groups, it is believed that the interparticle crosslinking agent reacts with the carboxyl groups of the polymer materials to form covalent chemical crosslink bonds between the polymer chains of different precursor particles. The covalent chemical crosslink bonds generally arise as a result of the formation of ester, amide (imide) or urethane groups by reaction of the functional groups of the crosslinking agents with the carboxyl groups of the polymer material. In preferred executions, it is believed that ester bonds are formed. Thus, preferred interparticle crosslinking agents are those agents capable of reacting with the carboxyl groups in the preferred polymers to form ester bonds.

Interparticle crosslinking agents useful in the present invention are those that react with the polymer material of the precursor particles used to form the interparticle crosslinked aggregates. Suitable interparticle crosslinking agents may comprise a number of different agents such as, for example, compounds having at least two polymerizable double bonds; compounds having at least one polymerizable double bond and at least one functional group reactive with the polymer material; compounds having at least two functional groups reactive with the polymer material; polyvalent metal compounds; or monomers as described herein. Specific crosslinking agents useful in the present invention are described in the hereinbefore referenced U.S. Pat. No. 4,076,663 and U.S. Pat. No. Re. 32,649 which are incorporated herein by reference.

Where carboxyl groups are present on or in the polymer materials (i.e., the polymer chains) of the precursor particles, preferred interparticle crosslinking agents possess at least two functional groups per molecule capable of reacting with the carboxyl group. Preferred interparticle crosslinking agents include polyhydric alcohols such as ethylene glycol, diethylene glycol, triethylene glycol, tetraethylene glycol, polyethylene glycol, glycerol (1,2,3-propanetriol), polyglycerol, propylene glycol, 1, 2-propanediol, 1, 3-propanediol, trimethylol propane, diethanolamine, triethanolamine, polyoxypropylene oxyethylene-oxypropyle block copolymer, sorbitan fatty acid esters, polyexyethylene sorbitan fatty acid esters, pentaerythritol, and sorbitol; polyglycidyl ether compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and propylene glycol diglycidyl ether; polyaziridine compounds such as 2, 2-bishydroxymethyl butanol-tris[3-(i-aziridine) propionate], 1, 6-hexamethyl tolulene diethylene urea, and diphenyl methane-bis-4, 4'-N,N'-diethylene urea; haloepoxy compounds such as epichlorohydrin and α-methylfluorohydrin; polyaldehyde compounds such as glutaraldehyde and glyoxazole; polyamine compounds such as ethylene diamine, diethylene triamine, triethylene tetramine, tetraethylene pentamine, pentaethylene hexamine, and polyethylene imine; and polyisocyanate compounds such as 2, 4-toluene diisocyanate and hexamethylene diisocyanate.

One interparticle crosslinking agent or two or more substantially mutually unreactive interparticle crosslinking agents selected from the group mentioned above may be used. Particularly preferred interparticle crosslinking agents for use herein with carboxyl-containing polymer chains are ethylene glycol; glycerol; trimethylol propane; 1, 2-propanediol; and 1, 3-propanediol.

The proportion of the interparticle crosslinking agent to be used in the present invention is in the range of from about 0.01 parts to about 30 parts by weight, preferably from about 0.5 parts to about 10 parts by weight, most preferably from about 1 part to about 5 parts by weight, per 100 parts by weight of the precursor particles.

In the present invention, other materials or agents can be used with the interparticle crosslinking agent(s) as an aid in producing the interparticle crosslinked aggregates or in promoting or assisting in the reaction of the interparticle crosslinking agent with the polymer material of the precursor particles.

For example, water may be used in conjunction with the interparticle crosslinking agent. The water functions to promote uniform dispersion of the interparticle crosslinking agent on the surface of the precursor particles and permeation of the interparticle crosslinking agent into the surface region of the precursor particles. The water also promotes stronger physical association between the precursor particles of the prereacted aggregates, and the dry and swollen integrity of the resultant interparticle crosslinked aggregates. In the present invention, the water is used in a proportion of less than about 20 parts by weight (0 parts to about 20 parts by weight), preferably in the range of from about 0.01 parts to about 20 parts by weight, more preferably in the range of from about 0.1 parts to about 10 parts by weight, based on 100 parts by weight of the precursor particles. The actual amount of water to be used will vary depending upon the kind of polymer material and the particle size of the precursor particles.

Organic solvents may also be used in conjunction with the interparticle crosslinking agent. The organic solvents are used to promote uniform dispersion of the interparticle crosslinking agent on the surface of the precursor particles. The organic solvents are preferably hydrophilic organic solvents. The hydrophilic organic solvents useful in the present invention include lower alcohols such as methanol, ethanol, n-propanol, isopropanol, n-butanol, isobutanol, sec-butanol and t-butanol; ketones such as acetone, methylethyl ketone, and methylisobutyl ketone; ethers such as dioxane, tetrahydrofuran, and diethyl ether; amides such as N,N-dimethylformamide and N,N-diethylformamide; and sulfoxides such as dimethyl sulfoxide. The hydrophilic organic solvent is used in the present invention in a proportion of less than about 60 parts by weight (0 parts to about 60 parts by weight), preferably in the range of from about 0.01 parts to about 60 parts by weight, more preferably from about 1 part to about 20 parts by weight, based on 100 parts by weight of the precursor particles. The actual amount of hydrophilic organic solvent to be used will vary depending upon the kind of polymer material and the particle size of the precursor particles.

The interparticle crosslinking agent may also be used in a mixture with water and one or more hydrophilic organic solvents. It has been found that the use of a water/interparticle crosslinking agent solution provides the greatest penetration of the crosslinker into the surface region of the precursor particles while a solution of hydrophilic organic solvent/interparticle crosslinking agent provides minimal penetration of the crosslinker. However, a mixture of all three agents is preferred in order to control the amount of the penetration of the interparticle crosslinking agent into the surface region of the precursor particles. Specifically, it has been found that the higher the water to organic solvent component ratio, the deeper the crosslinker penetration, the greater the fluid stability of the aggregates under stress, and the greater the reduction in the resultant absorptive capacity of the interparticle crosslinked aggregates. Typically, the ratio of water to hydrophilic organic solvent in the solution will be in the range of from about 10:1 to about 1:10. The hydrophilic organic solvent/water/interparticle crosslinking agent solution is used in a proportion less than about 60 parts by weight (0 parts to about 60 parts by weight), preferably in the range of from about 0.01 parts to about 60 parts by weight, more preferably from about 1 part to about 20 parts by weight, based on 100 parts by weight of the precursor particles.

Other optional components may also be mixed with the solution containing the interparticle crosslinking agent. For example, an initiator, a catalyst, or non-acid co-monomer materials may be added. Examples of these materials suitable for use herein are described in the hereinbefore referenced U.S. Pat. No. Re. 32,649.

The method of producing polymeric compositions containing interparticle crosslinked aggregates involves providing precursor particles of the type herein described; applying an interparticle crosslinking agent onto the precursor particles; physically associating the precursor particles to form a multiplicity of aggregates; and reacting the interparticle crosslinking agent with the polymer material of the precursor particles of the aggregates, while maintaining the physical association of the precursor particles, to form crosslink bonds between the precursor particles.

The interparticle crosslinking agent is applied onto the precursor particles. The interparticle crosslinking agent may be applied by any of various techniques and apparatus used for applying solutions to materials including coating, dumping, pouring, dropping, spraying, atomizing, condensing, or immersing the interparticle crosslinking agent on the precursor particles. As used herein, the term "applied onto" means that at least a portion of the surface area of at least one of the precursor particles to be joined per aggregate has the interparticle crosslinking agent coated on it. Thus, the interparticle crosslinking agent may be applied onto only some of the precursor particles, onto all of the precursor particles, onto only a portion of the surface of some or all of the precursor particles, or onto the entire surface of some or all of the precursor particles. Preferably, the interparticle crosslinking agent is coated onto the entire surface of most, preferably all, of the precursor particles so as to enhance the efficiency, strength, and density of the interparticle crosslink bonds between the precursor particles.

In the preferred embodiments of the present invention, after the interparticle crosslinking agent has been applied onto the precursor particles, the interparticle crosslinking agent is mixed with the precursor particles by any of a number of mixing techniques to insure that the precursor particles are thoroughly coated with the interparticle crosslinking agent. Because the precursor particles are thoroughly coated with the interparticle crosslinking agent, the efficiency, strength, and density of the crosslink bonds between the precursor particles are enhanced. The mixing can be accomplished using various techniques and apparatus, including various mixers or kneaders, as are known in the art.

Before, during, or after applying the interparticle crosslinking agent onto the precursor particles, the precursor particles are physically associated together to form a multiplicity of aggregates. The term "physically associated" is used herein to mean that the precursor particles are brought together and remain in contact with each other as component parts in any of a number of various ways and spatial relationships so as to form single units (aggregates).

The precursor particles are preferably physically associated together by applying an associating agent onto the precursor particles and physically contacting the precursor particles at at least the portion of the surface of the precursor particles having the associating agent applied thereto. Preferred associating agents cause the polymer material of the precursor particles, when brought together, to adhere together by the action of fluid surface tension forces and/or the entanglement of polymer chains due to external swelling. Associating agents useful in the present invention include hydrophilic organic solvents, typically low molecular weight alcohols such as methanol, ethanol, or isopropanol ; water; a mixture of hydrophilic organic solvents and water; certain interparticle crosslinking agents as hereinbefore described; volatile hydrophobic organic compounds such as hexane, octane, benzene or toluene; or mixtures thereof. Preferred associating agents are water, methanol, isopropanol, ethanol, interparticle crosslinking agents such as glycerol, or mixtures thereof. Typically, the associating agent comprises a mixture including an interparticle crosslinking agent such that the step of applying an interparticle crosslinking agent is carried out simultaneously with the step of applying an associating agent.

The associating agents may be applied to the precursor particles by any of various techniques and apparatus used for applying solutions to materials including coating, dumping, pouring, spraying, atomizing, condensing or immersing the associating agent on the precursor particles. The associating agent is applied onto at least a portion of the surface area of at least one of the precursor particles to be joined per aggregate. Preferably, the associating agent is coated onto the entire surface of most, preferably all, of the precursor particles. The associating agent is generally mixed with the precursor particles by any of a number of mixing techniques and mixing apparatus to insure that the precursor particles are thoroughly coated with the associating agent.

When an associating agent has been applied to the precursor particles, the precursor particles may be physically contacted together in a number of different ways. For example, the associating agent alone may hold the particles together in contact. Alternatively, gravitational forces may be used to insure contact between the precursor particles. Further, the particles may be placed in a container having a fixed volume so as to insure contact between the precursor particles.

The precursor particles can alternatively be physically associated together by physically constraining the precursor particles such that they are in contact with each other. For example, the precursor particles may be packed tightly into a fixed container having a fixed volume such that the precursor particles physically contact each other. Alternatively or in combination with the above procedure, gravitational forces may be used to physically associate the precursor particles. The precursor particles may also be physically associated together via electrostatic attraction or by the introduction of an adhering agent (e.g., an adhesive material such as a water-soluble adhesive) to adhere them together. The precursor particles may also be attached to a third member (a substrate) such that the precursor particles are brought into contact with each other by the substrate.

The precursor particles may be associated together in various spatial relationships to form aggregates having a variety of resultant shapes and sizes. For example, one or more precursor particles may be associated to a central or core precursor particle; the precursor particles may be randomly associated so that a given precursor particle is associated with one, two, or more precursor particles; or the precursor particles may be associated in a defined plane, shape, or geometric pattern.

While the precursor particles may be brought together in a number of various spatial relationships, the precursor particles at least need to be contacted at their surfaces to which the interparticle crosslinking agent(s) and/or associating agent(s) were or will be applied. Typically, the interparticle crosslinking agent or associating agent is coated over the entire surface of the precursor particles such that they can be associated at any location on their surfaces. However, if the interparticle crosslinking agent or associating agent is applied to only a portion of the surface of one or more of the precursor particles, steps must be taken to insure that the precursor particles are associated together at this surface.

Simultaneously or after the interparticle crosslinking agent has been applied and the precursor particles have been associated together, the interparticle crosslinking agent is reacted with the polymer material of the precursor particles of the aggregates, while maintaining the physical association of the precursor particles, to form crosslink bonds between the precursor particles to form interparticle crosslinked aggregates.

The reaction between the interparticle crosslinking agent and the polymer material must be activated and completed to form the crosslink bonds between different precursor particles to form the interparticle crosslinked aggregates. Although the crosslinking reaction may be activated by irradiation (e.g., ultraviolet, gamma-, or X-radiation) or by a catalyst, the crosslinking reaction is preferably thermally activated (heating). Heating activates and drives the reaction and drives off any volatiles present in the mixture. Such reaction conditions will generally involve heating the associated precursor particles and the interparticle crosslinking agent for certain times and at certain temperatures. The heating step can be carried out using a number of different apparatus as are known including the various ovens or driers as are known in the art.

Generally, the reaction is effected by heating to a temperature above about 90° C. for sufficient time to complete the crosslinking reaction. For each set of specific interparticle crosslinking agent(s) and polymer materials of the precursor particles used, if the temperature is too low or the time is too short, the reaction will not be sufficiently driven resulting in fewer and weaker interparticle crosslink bonds and a desired quantity of interparticle crosslinked aggregates will not be produced. If the temperature is too high, the absorbency of the precursor particles may be degraded or the network crosslinks of these precursor particles, depending upon the specific polymer materials, may be degraded to such a point that the resultant aggregates are not useful for absorbing large quantities of liquids. In addition, if the time and temperatures are not correct, the extractable levels of the resultant aggregates may increase, thereby increasing the incidence of that form of gel blocking. Therefore, the reaction will generally be carried out at a temperature in the range from about 120° C. to about 300° C., more preferably from about 150° C. to about 250° C.

The reaction between the interparticle crosslinking agent and the polymer material of the precursor particles is carried out until the reaction is completed. The time for completion of the reaction will vary depending upon the specific crosslinking agents, polymer materials, additives, and the reaction conditions and apparatus chosen. One method of determining if the reaction is complete is to measure the drop in the Absorptive Capacity of the polymeric composition versus the original Absorptive Capacity of the precursor particles. It has been found that the reaction is generally complete when the Absorptive Capacity of the polymeric composition has dropped between about 5% and about 70%. (While an ideal situation would be that the Absorptive Capacity of the polymeric composition would not decrease, it is believed that the formation of crosslink bonds reduces the Absorptive Capacity such that the higher the drop in Absorptive Capacity, the higher the strength and number of the resultant aggregates.) More specifically, the completion of the reaction may be satisfied by the following equation:

$$30 \leq (100+R)Q/P \leq 95$$

wherein P is the Absorptive Capacity of the precursor particles; Q is the Absorptive Capacity of the reaction product, and R is the amount, in parts by weight, of the interparticle crosslinking agent used per 100 parts by weight of the precursor particles. In certain embodiments, the Absorptive Capacity drop will be between about 15% and about 60%. Thus, for the present invention, the time to complete the reaction, in the absence of catalysts, will generally be from about 5 minutes to about 6 hours, more preferably from about 10 minutes to about 3 hours to effect the Absorptive Capacity drop as defined above.

For the preferred polymer material of the precursor particles, slightly network crosslinked products of partially neutralized polyacrylic acid, and the preferred interparticle crosslinking agents, such as glycerol or trimethylol propane, such reaction conditions will involve a temperature of from about 170° C. to about 220° C. for about 2 hours to about 20 minutes, respectively. More preferably, the reaction is carried out at a temperature between about 190° C. to about 210° C. for about 45 minutes to about 30 minutes, respectively. The actual time and temperatures used will vary depending upon the specific polymer materials used for the precursor particles, the specific interparticle crosslinking agents used, and the presence or absence of a catalyst used to drive the reaction.

The crosslinking reaction can be promoted by adding an initiator and/or a catalyst to the interparticle crosslinking agent to reduce the time and/or the temperature and/or the amount of interparticle crosslinking agent required to join the precursor particles together. Generally, however, the reaction is conducted in the absence of a catalyst.

The physical association of the precursor particles needs to be maintained during the reaction step so that the interparticle crosslinked aggregates of the present invention are formed in especially high percentages. If forces or stresses sufficient to dissociate the precursor particles are present during the reaction step, crosslink bonds between the precursor particles (interparticle crosslink bonds) may not be formed. The physical association of the precursor particles is typically maintained by insuring minimal dissociation forces or stresses are introduced during the reaction step.

As an optional and preferred step in the method of forming the polymeric compositions comprising interparticle crosslinked aggregates, at least the interparticle crosslinked aggregates and, preferably, the remaining nonaggregate particles of the polymeric composition, are surface treated. For example, U.S. Pat. No. 4,824,901 issued to Alexander et al. on Apr. 25, 1989, discloses the surface treatment of polymeric particles with a polyquaternary amine. In an exemplary method, the polymer material existing at least in the vicinity of the surface of the precursor particles is surface crosslinked such as disclosed in U.S. Pat. No. 4,666,983, entitled "Absorbent Article" issued to Tsubakimoto et al. on May 19, 1987; and U.S. Pat. No. 4,734,478, entitled "Water Absorbing Agent" issued to Tsubakimoto et al. on Mar. 29, 1988; which patents are incorporated herein by reference. By utilizing a surface crosslinking step in the present invention, the resistance to deformation of the resultant interparticle crosslinked aggregates, and thus the polymeric composition, when swollen, is improved. Preferably, the interparticle crosslinking agent applied to the precursor particles also serves as the surface crosslinking agent such that the interparticle crosslinked aggregates are preferably simultaneously formed and surface crosslinked.

As previously discussed, the steps in the method for producing the interparticle crosslinked aggregates need not be carried out in any specific order. In addition, the steps may be carried out simultaneously. Hereinafter, exemplary methods using the above-identified steps will be set forth.

In a preferred embodiment, the interparticle crosslinking agent is applied onto the precursor particles while the precursor particles are simultaneously physically associated together to form a multiplicity of aggregates. The interparticle crosslinking agent is subsequently reacted with the aggregates of the associated precursor particles, either immediately after the above steps are completed or after the mixture has been left standing for a period of time, to simultaneously form and surface crosslink the interparticle crosslinked aggregates. Typically, the precursor particles are mixed with a mixture of an interparticle crosslinking agent, water, and a hydrophilic organic solvent. The solution of the interparticle crosslinking agent, water, and the hydrophilic organic solvent also serves as an associating agent for the precursor particles. The interparticle crosslinking agent also preferably serves as a surface crosslinking agent. The precursor particles are physically associated together while the mixture is applied thereto. The crosslinking agent is subsequently reacted with the aggregates of the associated precursor particles by heating at a sufficient temperature for a sufficient time to form crosslink bonds between different precursor particles and simultaneously to surface crosslink the resultant interparticle crosslinked aggregates and a significant portion, if not all, of any remaining nonaggregated particles of the polymeric composition.

In an alternative embodiment, the interparticle crosslinking agent is applied onto the precursor particles; the precursor particles are subsequently physically associated together; and the interparticle crosslinking agent is subsequently reacted with the precursor particles to form interparticle crosslinked aggregates.

In another alternative embodiment, the precursor particles are associated together, an interparticle crosslinking agent is subsequently applied onto the associated precursor particles, and the interparticle crosslinking agent is subsequently reacted with the precursor particles to form interparticle crosslinked aggregates.

In a further alternative embodiment, the steps are performed simultaneously such that interparticle crosslinked aggregates are produced.

The interparticle crosslinked aggregates of the present invention should be present in the polymeric composition in an amount sufficient to provide the benefits discussed herein. A method for determining whether sufficient quantities of interparticle crosslinked aggregates are present in the polymeric composition is to determine the shift in mass average particle size between the precursor particles and the resultant polymeric composition. Preferably, the shift in mass average particle size should be such that the resultant polymeric composition has a mass average particle size at least about 25%, preferably about 30%, more preferably about 40%, most preferably about 50%, greater than the mass average particle size of the precursor particles. In preferred embodiments of the present invention, the mass average particle size of the precursor particles is less than about 1000 microns, more preferably less than about 600 microns, most preferably less than about 500 microns.

In especially preferred embodiments of the present invention, the mass average particle size of the precursor particles is relatively small (i.e., the precursor particles are fines). It has been found that the use of large amounts of fine precursor particles forms interparticle crosslinked aggregates having especially high surface area to mass ratios so as to have high swelling rates. FIG. 14 shows an embodiment of such a polymeric composition while FIG. 15 shows an interparticle crosslinked aggregate comprising such fine precursor particles. In these especially preferred embodiments, the mass average particle size of the precursor particles is less than about 300 microns. In preferred embodiments, the mass average particle size of the precursor particles is less than about 180 microns, less than about 150 microns, or less than about 106 microns. In an exemplary embodiment, at least about 90% of the precursor particles have a particle size less than about 300 microns, more preferably less than about 150 microns. Since the interparticle crosslinked aggregates formed from such small precursor particles typically comprise many precursor particles, the shift in mass average particle size is much greater than the shifts using larger precursor particles. The shift in mass average particle size is such that the resultant polymeric composition has a mass average particle size at least about 50%, preferably at least about 75%, more preferably at least about 100%, most preferably at least about 150%, greater than the mass average particle size of the precursor particles.

The amount of interparticle crosslinked aggregates within the polymeric composition may also be defined in terms of the percent by weight of the interparticle crosslinked aggregates within the polymeric composition. For the preferred polymeric compositions of the present invention, at least about 25% by weight of the particles of the polymeric composition, more preferably at least about 30% by weight, most preferably at least about 40% by weight, comprise interparticle crosslinked aggregates. In the most preferred embodiments, at least about 50% by weight, more preferably at least about 75% by weight, and most preferably at least about 90% by weight, of the particles of the polymeric composition comprise interparticle crosslinked aggregates.

An indication that crosslink bonds are being formed between the previously independent precursor particles is that the resultant interparticle crosslinked aggregates are generally fluid (i.e., liquid) stable. "Fluid stable" is used herein to mean an aggregate unit that upon contact with or swelling (with and/or without stress) in an aqueous fluid remains substantially intact (i.e., at least two of the previously independent component precursor particles remain joined together). While the definition of fluid stability recognizes that at least two of the precursor particles remain joined together, preferably all of the precursor particles used to make up the specific interparticle crosslinked aggregate remain joined together. However, it should be recognized that some of the precursor particles may dissociate themselves from the interparticle crosslinked aggregate if, for example, certain particles have been subsequently water agglomerated to the interparticle crosslinked aggregate.

Fluid stability of the interparticle crosslinked aggregates of the present invention allows the interparticle crosslinked aggregate to maintain its structure in both the dry and wet (swollen) state, to immobilize the component precursor particles to minimize migration of the particles, and to maintain a rapid rate of fluid uptake. In an end product such as an absorbent member, fluid stability is beneficial in reducing gel blocking since the precursor particles remain aggregated even when contacted with excess liquids, in allowing one to use previously independent fine particles in an aggregated form, and in increasing the rate of fluid uptake of the resultant polymeric composition while minimizing the incidence of gel blocking. Further, the larger particles of the interparticle crosslinked aggregates open the absorbent member's capillary channels providing improved liquid handling characteristics.

The fluid stability of aggregates can be determined by a two step process. The initial dynamic response of the aggregate unit upon contact with an aqueous fluid (Synthetic Urine) is observed and then the fully swollen equilibrium condition of the aggregate is observed. A test method for determining fluid stability based on these criteria is hereinafter described in the Test Methods section.

As previously noted, the interparticle crosslinked aggregates maintain their structural integrity even when swollen. This structural integrity can be measured in terms of the gel expansion pressure of the sample. The gel expansion pressure of a polymeric composition relates to the ability of a sample of a partially swollen, particulate, absorbent, polymeric composition to maintain its structural integrity by resisting deformation and spreading. The gel expansion pressure can vary depending upon the particle size, the solution used for swelling the polymer material, the relative amount of Synthetic Urine absorbed (e.g., the "X-load"), and the geometry of the test apparatus. The X-load refers to the number of grams of Synthetic Urine added per gram of the particulate, absorbent, polymeric composition. Gel Expansion Pressure as used herein is defined in terms of the net force exerted by a partially swollen polymer material in attempting to regain, via elastic response, its relative dry state structural geometry when it is volumetrically constrained in its partially swollen state. It has been found desirable to utilize in absorbent members those particles which have as high a Gel Expansion Pressure as possible to minimize gel blocking and promote fluid distribution within the structure. Gel Expansion Pressure is measured in terms of kilodynes per square centimeter. A procedure for determining the Gel Expansion Pressure is described hereinafter in the Test Methods section.

The interparticle crosslinked aggregates provide a polymeric composition having a high rate of fluid uptake as measured by their swelling rate. The swelling rate of a polymeric composition refers to the average rate of fluid uptake of a given amount of Synthetic Urine by a sample of the polymeric composition. Swelling Rate as defined herein is a measure of the liquid diffusion rate in the absorbent polymer as modified by the permeability of the overall gel mass. Thus, the permeability of the gel mass can become the limiting factor by limiting how fast free fluid can get to other particles in the mixture. The Swelling Rate is measured and defined in terms of grams of Synthetic Urine per gram of polymer per second. The Swelling Rate may be determined by using a method described hereinafter in the Test Methods section.

Preferred particulate, absorbent, polymeric compositions comprising interparticle crosslinked aggregates of the present invention have a Gel Expansion Pressure at 30 minutes under a 28× load (i.e., as previously defined, 28 grams of Synthetic Urine added per gram of polymer) of greater than or equal to about 20 kilodynes per square centimeter, preferably greater than or equal to about 25 kilodynes per square centimeter. At a 15× load, the Gel Expansion Pressure at 30 minutes of preferred polymeric compositions is greater than or equal to about 45 kilodynes per square centimeter, more preferably greater than or equal to about 60 kilodynes per square centimeter. The Swelling Rate of the polymeric compositions of the present invention at a 28× load are preferably greater than or equal to about 0.3 g/g/sec, more preferably greater than or equal to about 0.5 g/g/sec. For especially preferred embodiments of the polymeric compositions of the present invention, the Swelling Rate at a 28× load is preferably greater than or equal to about 1.0 g/g/sec, more preferably greater than or equal to about 1.1 g/g/sec, most preferably greater than or equal to about 1.25 g/g/sec.

As previously noted, the surface area to mass ratio of a given particle is indicative of the rate of fluid uptake of the particle. The greater the surface area to mass ratio of the particle, the more area there is for diffusion of the liquid to be absorbed. Thus, particles having a higher surface area to mass ratio with similar gel expansion pressure characteristics (i.e., without a loss of high gel expansion pressure values) and other properties are preferred. The surface area to mass ratio is defined in a relationship of meters squared per gram of material. The surface area to mass ratio of a given polymeric composition may be determined in accordance with the method described hereinafter in the Test Methods section. In the particulate, absorbent, polymeric compositions of the present invention, the surface area to mass ratio of the interparticle crosslinked aggregates is higher than the surface area to mass ratio of nonaggregate particles of the same size such that the Swelling Rate of the polymeric compositions containing the interparticle crosslinked aggregates is increased. Further, the Swelling Rate of the interparticle crosslinked aggregates is generally higher that the Swelling Rate of the precursor particles forming the interparticle crosslinked aggregates.

Another feature of the polymeric compositions of the present invention which is especially useful in absorbent members and absorbent articles herein relates to the level of extractable polymer material present in such compositions. Extractable polymer levels can be determined by contacting a sample of the polymeric composition with Synthetic Urine for a substantial period of time (e.g., at least 16 hours) which is needed to reach extraction equilibrium, by then filtering the formed hydrogel from the supernatent liquid, and finally by then determining the polymer content of the filtrate. The procedure used to determine the extractable polymer content of polymer materials is set forth in the hereinbefore-referenced U.S. Pat. Re. No. 32,649. Polymeric compositions having an equilibrium extractables content in Synthetic Urine of no more than about 17%, preferably no more than about 10%, by weight of the polymer material are especially preferred herein.

In use, the particulate, absorbent, polymeric compositions comprising interparticle crosslinked aggregates are contacted with liquids such that the particles will swell and absorb such liquids. Generally, the interparticle crosslinked aggregates of the present invention will swell generally isotropically, even under moderate confining pressures, such that the interparticle crosslinked aggregate will maintain its relative geometry and spatial relationships even when swollen. The precursor particles forming the interparticle crosslinked aggregate will not dissociate upon contact with or swelling in the liquid to be absorbed (i.e., the interparticle crosslinked aggregates are "fluid stable") such that fine particles will not break off and gel block the acquisition of the liquids. Further, the interparticle crosslinked aggregates have relatively high rates of fluid uptake to provide rapidly acquiring materials due to the high surface area to mass ratio of the interparticle crosslinked aggregates.

While the use of the polymeric compositions herein is specifically discussed in terms of their use in absorbent products, absorbent members, and absorbent articles, it should be understood that the particulate, absorbent, polymeric compositions comprising interparticle crosslinked aggregates can be used for many purposes in many other fields of use. For example, the polymeric compositions of the present invention can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials.

Figure 16:
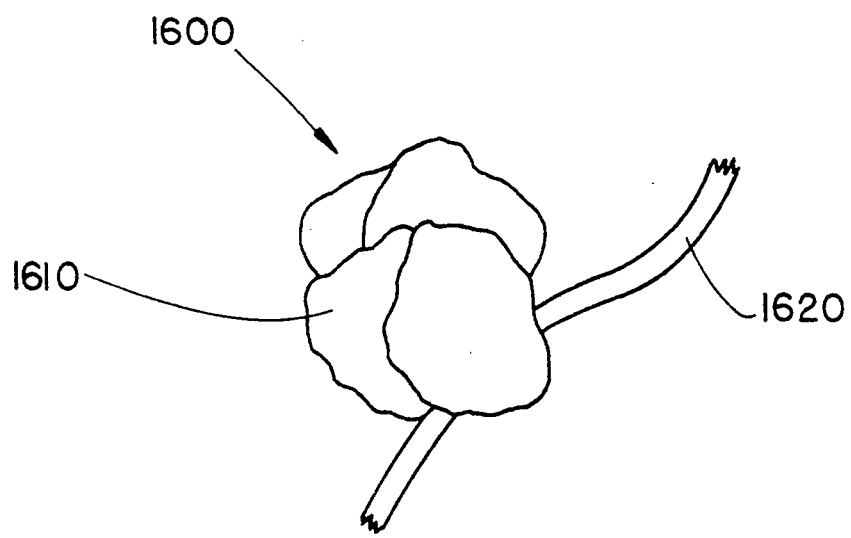
FIG. 16 is a perspective view of an absorbent product of the present invention comprising a carrier and an interparticle crosslinked aggregate of the present invention joined to the carrier.

The interparticle crosslinked aggregates or the polymeric compositions comprising interparticle crosslinked aggregates of the present invention are useful when joined to a carrier. FIG. 16 shows an embodiment of an absorbent product 1600 wherein an individual interparticle crosslinked aggregate 1610 is joined to a carrier 1620. Carriers 1620 useful in the present invention include absorbent materials such as cellulose fibers. The carriers 1620 also may be any other carriers as are known in the art such as nonwoven webs, tissue webs, foams, superabsorbent fibers such as polyacrylate fibers or FIBERSORB fibers (as available from the Arco Chemical Company of Wilmington, Del.), apertured polymeric webs, a modified cellulose film, woven webs, synthetic fibers, metallic foils, elastomers, and the like. The interparticle crosslinked aggregate 1610 may be joined directly or indirectly to the carriers 1620 and may be joined thereto via chemical or physical bonding such as are known including adhesives or chemicals that react to adhere the interparticle crosslinked aggregate 1610 to the carriers 1620.

As shown in FIGS. 1–11, the particulate, absorbent, polymeric compositions of the present invention comprising interparticle crosslinked aggregates, whether as broadly defined or of the "preferred" or "especially preferred" types as hereinbefore described, can be employed in combination with fibrous material to form improved absorbent products such as absorbent members. The absorbent members of the present invention will be described herein in relationship to their use in absorbent articles; however, it should be understood that the potential application of the absorbent members should not be limited to absorbent articles.

The absorbent members of the present invention are generally compressible, conformable, non-irritating to the skin, and capable of absorbing and retaining liquids and certain body exudates. It should be understood that for purposes of this invention that an absorbent member is not necessarily limited to a single layer or sheet of material. Thus, an absorbent member may actually comprise laminates, webs, or combinations of several sheets or webs of the types of materials as hereinafter described. Thus, as used herein, the term "member" includes the term "members" or "layers" or "layered." Preferred absorbent members of the present invention are webs or batts which comprise entangled masses of fibers (fibrous or fiber material) and the particulate, absorbent, polymeric compositions comprising interparticle crosslinked aggregates of the present invention. The absorbent members most preferably comprise a web of a mixture of fiber material and specific quantities of the particulate, absorbent, polymeric composition comprising interparticle crosslinked aggregates as described herein.

Various types of fiber material can be used in the absorbent members of the present invention. Any type of fiber material which is suitable for use in conventional absorbent products is also suitable for use in the absorbent members herein. Specific examples of such fiber materials include cellulose fibers, modified cellulose fibers, rayon, polypropylene, and polyester fibers such as polyethylene terephthalate (DACRON), hydrophilic nylon (HYDROFIL), and the like. Other fiber materials include cellulose acetate, polyvinyl fluoride, polyvinylidene chloride, acrylics, polyvinyl acetate, polyamides (such as nylon), bicomponent fibers, tricomponent fibers, mixtures thereof, and the like. Hydrophilic fiber materials are preferred. Examples of suitable hydrophilic fiber materials in addition to some already mentioned are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent products, are suitable for use in the absorbent members of the present invention by virtue of their good wicking properties. This is because, in the structures herein, the wicking propensity of the fibers is as important, if not more important, than the absorbent capacity of the fiber material itself due to the high rate of fluid uptake and lack of gel blocking properties of the particulate, absorbent, polymeric compositions of the present invention employed in such absorbent members. Hydrophobic synthetic fibers can also be used, but are less preferred.

For reasons of availability and cost, cellulose fibers are generally preferred for use herein as the hydrophilic fiber material of the absorbent members. Most preferred are wood pulp fibers which are also referred to as airfelt.

Other cellulosic fiber materials which may be useful in certain absorbent members herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Types of stiffened, twisted, curled cellulosic fibers useful as the hydrophilic fiber material of the absorbent members herein are described in greater detail in U.S. Pat. No. 4,822,453 entitled "Absorbent Structure Containing Individualized Crosslinked Fibers, issued to Dean et al. on Apr. 18, 1989; U.S. Pat. No. 4,888,093 entitled "Individualized, Crosslinked Fibers And Process For Making Said Fibers" issued to Dean et al. on December 19, 1989; U.S. Pat. No. 4,889,595 entitled "Process For Making Individualized, Crosslinked Fibers Having Reduced Residuals And Fibers Thereof", issued to Herron et al. on Dec. 26, 1989; U.S. Pat. No. 4,889,596 entitled "Process For Making Individualized Crosslinked Fibers And Fibers Thereof", issued to Schoggen et al. on Dec. 26, 1989; U.S. Pat. No. 4,889,597 entitled "Process For Making Wet-Laid Structures Containing Individualized Stiffened Fibers", issued to Bourbon et al. on Dec. 26, 1989; and U.S. Pat. No. 4,898,642 entitled "Twisted, Chemically Stiffened Cellulosic Fibers And Absorbent Structures Made Therefrom", issued to Moore et al. on Feb. 6, 1990. Each of these patents are incorporated herein by reference.

As used herein, the term "hydrophilic" describes fibers or the surfaces of fibers which are wetted by the liquids deposited onto the fibers (i.e., if water or aqueous body liquids readily spreads on or over the surface of the fiber without regard to whether or not the fiber actually imbibes fluid or forms a gel). The state of the art respecting wetting of materials allows definition of hydrophobicity (and wetting) in terms of contact angles and the surface tension of the liquids and solids involved. This is discussed in detail in the American Chemical Society Publication entitled "*Contact Angle, Wettability, and Adhesion*" edited by Robert F. Gould and copyrighted in 1964. A fiber or surface of a fiber is said to be wetted by a liquid either when the contact angle between the liquid and the fiber or surface is less than 90° or when the liquid will tend to spread spontaneously across the surface of the fiber; both conditions normally coexisting.

The relative amount of fiber material and particulate, absorbent, polymeric composition used in the absorbent members of the present invention can be most conveniently expressed in terms of a weight percentage of the absorbent member. The absorbent members preferably contain from about 2% to about 98%, more preferably from about 5% to about 75%, and most preferably from about 10% to about 60%, by weight of the absorbent member, of the particulate, absorbent, polymeric composition. This concentration of the particulate, absorbent, polymeric composition can be expressed in terms of a weight ratio of fiber to particulate. This ratio may range from about 98:2 to about 2:98. For most absorbent members, the optimum fiber-to-particulate weight ratio is in the range of from about 95:5 to about 25:75, most preferably from about 90:10 to about 40:60.

In addition, the particulate, absorbent, polymeric composition may be dispersed in various weight ratios throughout different regions and thicknesses of the absorbent member. For example, the mixture of fiber material and the particulate, absorbent, polymeric composition may be disposed only in certain portions of the absorbent member. Preferably, the absorbent member contains a uniformly distributed mixture of hydrophilic fiber material and the particulate, absorbent, polymeric composition. The polymeric composition may be substantially uniformly dispersed (thoroughly dispersed) throughout the entire absorbent member as disclosed in U.S. Pat. No. 4,610,678 entitled "High-Density Absorbent Structures" issued to Paul T. Weisman and Stephen A. Goldman on Sep. 9, 1986, which patent is incorporated herein by reference. The polymeric composition may alternatively be distributed in regions or zones which have higher concentrations of the polymeric composition than do other regions or zones. For example, U.S. Pat. No. 4,699,823 issued to Kellenberger et al. on Oct. 13, 1987, discloses an absorbent member having the particulate, absorbent, polymeric composition distributed in a positive gradient through at least a portion of the thickness of the absorbent member. Preferably, the concentration gradient along the thickness dimension has the lowest concentration at or near the surface of the absorbent member which receives liquids (i.e., the top surface) and the highest concentration at or near the back surface of the absorbent member. This patent is incorporated herein by reference.

As indicated above, the particulate, absorbent, polymeric compositions of the present invention can have a particle size varying over a wide range. However, in the use of absorbent members, other considerations may preclude the use of very small or very large particles. For reasons of industrial hygiene, particles having a particle size less than about 30 microns are less desirable. Particles having a particle size larger than about 2 millimeters are also not desirable because they may cause a feeling of grittiness in the absorbent member which is undesirable from a consumer aesthetic standpoint. Preferred for use herein are particles having a particle size of from about 45 microns to about 1000 microns.

The density of the absorbent members herein can be of some importance in determining the absorbent properties of the absorbent members and of the absorbent articles in which such absorbent members are employed. The density of the absorbent members herein will generally be in the range of from about 0.06 g/cm$^3$ to about 0.5 g/cm$^3$, and more preferably within the range of from about 0.09 g/cm$^3$ to about 0.30 g/cm$^3$. Density values for these structures are calculated from their basis weight and caliper. Caliper is measured under a "gentle" load of 10 grams/cm$^2$. The basis weight is measured by die-cutting a certain size sample and weighing the sample on a standard scale, the weight and area of the sample determining the basis weight. The density and basis weight values include the weight of the particles of the polymeric composition.

The absorbent members herein can contain a variety of optional materials in addition to the fiber materials and the polymeric composition components. Such optional materials can include, for example, fluid distribution aids, antimicrobials, pH control agents, odor control agents, perfumes, etc. If present, these optional components will generally comprise no more than about 30% by weight of the absorbent members herein.

The absorbent members herein comprising a mixture of fiber material and the particulate, absorbent, polymeric composition of the present invention can be prepared by any process or technique which provides a web comprising a combination of the fibers and the polymeric composition particles. Absorbent members of the present invention are preferably formed by air-laying a substantially dry mixture of fibers and polymeric composition particles and, if desired or necessary, densifying the resulting web. Such a procedure is described more fully in the hereinbefore referenced U.S. Pat. No. 4,610,678, incorporated herein by reference. As indicated in U.S. Pat. No. 4,610,678, the air-laid webs formed by this procedure will preferably comprise substantially unbonded fibers and will preferably have a moisture content of 10% or less. In preparing webs by an air-laying process or by any other conventional procedure, care should be taken in handling and transporting the polymeric composition particles so as to avoid breaking these particles down into smaller particles. This is true even when the particles are interparticle crosslinked aggregates, although the interparticle crosslinked aggregates have a relatively high structural integrity in the dry state.

In an alternative embodiment of the absorbent members of the present invention, the absorbent member comprises a laminate (a layered absorbent member) containing at least one, and optionally two or more, layers of dispersed particles of the polymeric composition. The laminates preferably comprise layers or webs of fibrous materials (preferably a sheet of absorbent material), such as tissue paper. Such layered absorbent structures are more fully described in U.S. Pat. No. 4,578,068 entitled "Absorbent Laminate Structure" issued to Timothy A. Kramer, Gerald A. Young and Ronald W. Kock on Mar. 25, 1986, which patent is incorporated herein by reference. Additional methods and apparatus for making such laminates are described in U.S. Pat. No. 4,551,191 entitled "Method For Uniformly Distributing Discrete Particles On A Moving Porous Web", issued to Ronald W. Kock and John A. Esposito on Nov. 5, 1985, which patent is incorporated herein by reference.

Figure 5:
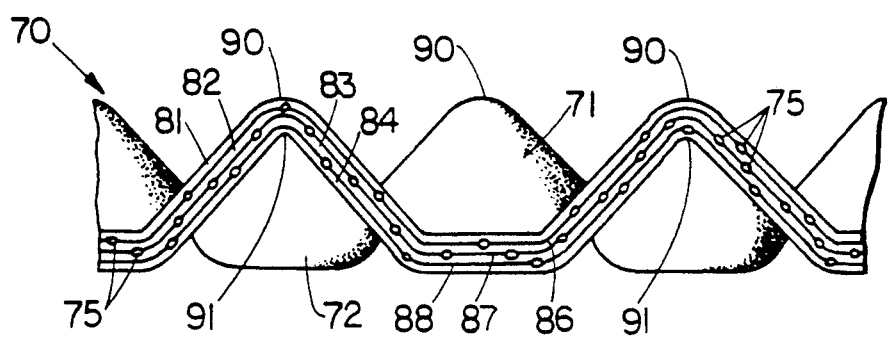
FIG. 5 is a fragmentary, enlarged cross-sectional view of a layered absorbent member (laminate) of the present invention.

FIG. 5 shows an exemplary embodiment of a laminate, layered absorbent member 70, of the present invention. Layered absorbent member 70 preferably comprises four webs of fibrous material: uppermost web 81, lowermost web 84, and intermediate webs 82 and 83. The layered absorbent member 70 has inner faces 86, 87 and 88 between adjacent webs with the particles 75 of the particulate, absorbent, polymeric composition of the present invention forming a discontinuous layer at each of the inner faces 86, 87 and 88. As shown in FIG. 5, the layered absorbent member 70 further preferably has conical protrusions 90 in the upper surface 71 and corresponding conical concavities 91 in the lower surface 72.

The layered absorbent members 70 of the present invention are produced comprising the following components: n substantially planar webs of fibrous materials, each of the webs having 2 substantially parallel surfaces, n being an integer of 2 or more; and particles of the particulate, absorbent, polymeric composition of the present invention. The layered absorbent members 70 of the present invention have an upper surface 71 and a lower surface 72. The layered absorbent members 70 comprise n webs of fibrous materials, n being an integer of two or more. The webs are layers such that there is an uppermost web 81, a lowermost web 84, n−2 intermediate webs 82, 83, and n−1 interfaces 86, 87, 88 of two opposed adjacent contacting surfaces of adjacent webs. Each of the interfaces has a surface area. The particles 75 of the polymeric composition form a discontinuous layer at one or more of the interfaces.

The layered absorbent members 70 of the present invention may have from two to a large number of webs of fibrous material. The number of webs is generally limited by the thickness of the webs. It is preferred that there be from about 2 to about 12 webs of fibrous material, more preferably from about 2 to about 5 webs of fibrous material. The particles 75 of the particulate, absorbent, polymeric composition may be provided between each adjacent web of fibrous material as shown in FIG. 5; however, the particles 75 may be included between only some of the adjacent webs of fibrous material.

As used herein, a web of fibrous material is a sheet of thin, substantially contiguous material having two substantially parallel surfaces. Although a web of fibrous material need not be flat or smooth, it is or can be laid out in a substantially planar, two-dimensional arrangement of indefinite length and indefinite width projecting in the two dimensions. Examples of webs of fibrous materials used in the layered absorbent members 70 of the present invention include many papers and nonwoven materials. The webs of fibrous materials used in the present invention are preferably webs of absorbent materials, more preferably webs of absorbent papers, most preferably absorbent tissue. The webs of fibrous materials may all be the same fibrous material or may be different fibrous materials.

In the layered absorbent members 70 of the present invention, the webs of fibrous materials are preferably frangibly bonded substantially entirely by fiber entanglement between contacting surfaces of adjacent webs at interfaces where the particles 75 are present. The particles may be immobilized at the interfaces by the fiber entrapment. Alternatively, the particles 75 of the polymeric composition may be bonded to one or more of the webs in several different manners. For example, a fine spray of glue may be deposited onto the webs to adhere the particles to the webs. Alternatively, the glue may be deposited onto the fibrous webs in a defined pattern, such as a spiral pattern, that adheres the webs of fibrous material together in a manner that forms pockets in which the particles are entrapped. Still further, the webs may be hydrogen bonded to the particles by spraying a mist of water onto the webs, adding the particles, compressing the webs together, and drying the resultant layered absorbent member. As shown in FIG. 5, the fibrous webs are preferably crimped between two crimping surfaces having mating z-direction geometrical protrusions and concavities to impart multiple z-direction protrusions 90 and concavities 91 to the layered stack of webs. An exemplary process for producing such layered absorbent members is described in the hereinbefore referenced U.S. Pat. No. 4,578,068.

An alternative embodiment of the layered absorbent members of the present invention is a "pouch" containing the particulate, absorbent, polymeric composition. The pouch is a layered absorbent member as described above wherein the number of fibrous webs equals two. The fibrous webs are joined to each other around their periphery so as to form a large pocket in the middle of the pouch. The particles of the polymeric composition are encased between the fibrous webs in the pocket. Thus, the pouch is similar to a tea bag in that the particulate, absorbent, polymeric composition is free to swell and absorb within the pouch. The fibrous webs of the pouch preferably comprise a nonwoven material as are known in the art with the nonwoven webs being heat sealed about their periphery, although other means for sealing the webs together as are known in the art, such as adhesives or ultrasonic bonds, may also be used.

Figure 1:
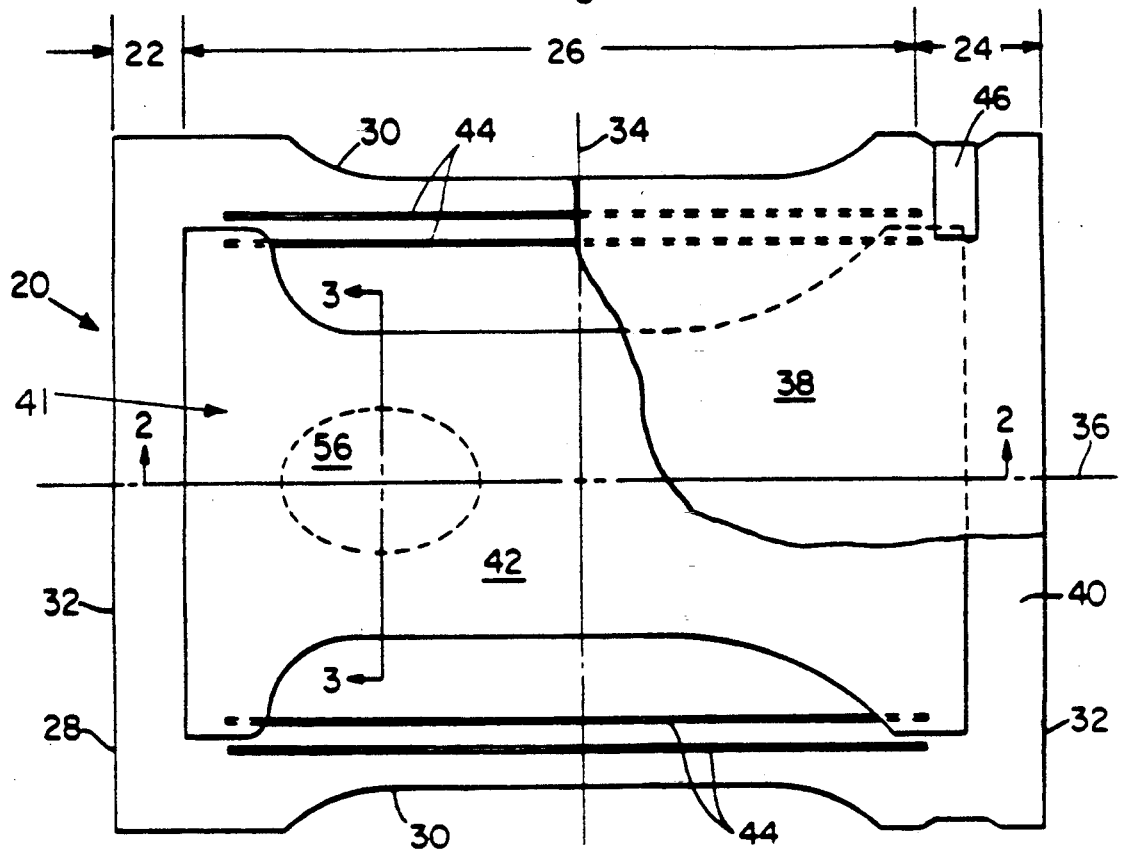
FIG. 1 is a plan view of a disposable diaper embodiment of the present invention wherein most of the topsheet has been cut-away to more clearly show the underlying absorbent core (an embodiment of an absorbent member of the present invention) of the diaper.

Because of the unique absorbent properties of the particulate, absorbent, polymeric compositions discussed herein, the absorbent members of the present invention are especially suitable for use as absorbent cores in absorbent articles, especially disposable absorbent articles. As used herein, the term "absorbent article" refers to articles which absorb and contain body exudates and more specifically refers to articles which are placed against or in proximity to the body of the wearer to absorb and contain the various exudates discharged from the body. Additionally, "disposable absorbent articles" are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of an absorbent article, diaper 20, is shown in FIG. 1. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like.

FIG. 1 is a plan view of the diaper 20 of the present invention in its flat-out, uncontracted state (i.e., with all the elastic induced contraction removed) with portions of the structure being cut-away to more clearly show the construction of the diaper 20 and with the portion of the diaper 20 which contacts the wearer facing the viewer. The diaper 20 is shown in FIG. 1 to have a front waistband region 22, a back waistband region 24, a crotch region 26, and a periphery 28 which is defined by the outer edges of the diaper in which the longitudinal edges are designated and the end edges are designated 32. The diaper additionally has a transverse centerline which is designated 34 and a longitudinal centerline which is designated 36.

The diaper 20 preferably comprises a liquid pervious topsheet 38; a liquid impervious backsheet 40 joined with the topsheet 38; an absorbent core 41 (absorbent member 42) positioned between the topsheet 38 and the backsheet 40; elastic members 44; and tape tab fasteners 46. While the topsheet 38, the backsheet 40, the absorbent core 41, and the elastic members 44 may be assembled in a variety of well known configurations, a preferred diaper configuration is described generally in U.S. Pat. No. 3,860,003 entitled "Contractable Side Portions For Disposable Diaper", which issued to Kenneth B. Buell on Jan. 14, 1975, and which patent is incorporated herein by reference. Alternatively preferred configurations for disposable diapers herein are also disclosed in U.S. Pat. No. 4,808,178 entitled "Disposable Absorbent Article Having Elasticized Flaps Provided With Leakage Resistant Portions" issued to Mohammed I. Aziz and Ted L. Blaney on Feb. 28, 1989; U.S. Pat. No. 4,695,278 entitled "Absorbent Article Having Dual Cuffs" issued to Michael I. Lawson on Sep. 22, 1987; and U.S. Pat. No. 4,816,025 entitled "Absorbent Article Having A Containment Pocket" issued to John H. Foreman on Mar. 28, 1989. These patents are incorporated herein by reference.

FIG. 1 shows a preferred embodiment of the diaper 20 in which the topsheet 38 and the backsheet 40 are coextensive and have length and width dimensions generally larger than those of the absorbent core 41. The topsheet 38 is associated with and superimposed on the backsheet 40 thereby forming the periphery 28 of the diaper 20. The periphery 28 defines the outer perimeter or the edges of the diaper 20. The periphery 28 comprises the longitudinal edges 30 and the end edges 32.

The diaper 20 has front and back waistband regions 22 and 24, respectively, extending from the end edges 32 of the diaper periphery 28 toward the transverse centerline 34 of the diaper a distance preferably about 5% of the length of the diaper 20. The waistband regions comprise the upper portions of the diaper 20, which, when worn, encircle the waist of the wearer. The crotch region 26 is that portion of the diaper 20 between the waistband regions 22 and 24, and comprises that portion of the diaper 20 which, when worn, is positioned between the legs of the wearer and covers the lower torso of the wearer. Thus, the crotch region 26 defines the area of typical liquid deposition for a diaper 20 or other disposable absorbent article.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which may be used to manufacture the topsheet 38. For example, the topsheet 38 may be woven, nonwoven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 40 is impervious to liquids and is preferably manufactured from a thin plastic film, although other flexible liquid impervious materials may also be used. The backsheet 40 prevents the exudates absorbed and contained in the absorbent core 41 from wetting articles which contact the diaper 20 such as bedsheets and undergarments. Preferably, the backsheet 40 is polyethylene film having a thickness from about 0.012 mm (0.5 mil) to about 0.051 centimeters (2.0 mils), although other flexible, liquid impervious materials may be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 41 while still preventing exudates from passing through the backsheet 40.

The size of the backsheet 40 is dictated by the size of the absorbent core 41 and the exact diaper design selected. In a preferred embodiment, the backsheet 40 has a modified hourglass-shape extending beyond the absorbent core 41 a minimum distance of at least about 1.3 centimeters to about 2.5 centimeters (about 0.5 to about 1.0 inch) around the entire diaper periphery 28.

The topsheet 38 and the backsheet 40 are joined together in any suitable manner. As used herein, the term "joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery 28 by attachment means (not shown) such as an adhesive or any other attachment means as known in the art. For example, a uniform continuous layer of adhesive, a patterned layer of adhesive, or an array of separate lines or spots of adhesive may be used to affix the topsheet 38 to the backsheet 40.

Tape tab fasteners 46 are typically applied to the back waistband region 24 of the diaper 20 to provide a fastening means for holding the diaper on the wearer. Only one of the tape tab fasteners is shown in FIG. 1. The tape tab fasteners 46 can be any of those well known in the art, such as the fastening tape disclosed in U.S. Pat. No. 3,848,594 issued to Kenneth B. Buell on Nov. 19, 1974, which patent is incorporated herein by reference. These tape tab fasteners 46 or other diaper fastening means are typically applied near the corners of the diaper 20.

The elastic members 44 are disposed adjacent the periphery 28 of the diaper 20, preferably along each longitudinal edge 30, so that the elastic members 44 tend to draw and hold the diaper 20 against the legs of the wearer. Alternatively, the elastic members 44 may be disposed adjacent either or both of the end edges 32 of the diaper 20 to provide a waistband as well as or rather than leg cuffs. For example, a suitable waistband is disclosed in U.S. Pat. No. 4,515,595 entitled "Disposable Diapers With Elastically Contractible Waistbands" which issued to David J. Kievit and Thomas F. Osterhage on May 7, 1985, which patent is herein incorporated by reference. In addition, a method and apparatus suitable for manufacturing a disposable diaper having elastically contractible elastic members is described in U.S. Pat. No. 4,081,301 entitled "Method and Apparatus for Continuously Attaching Discrete, Stretched Elastic Strands to Predetermined Isolated Portions of Disposable Absorbent Products" which issued to Kenneth B. Buell on Mar. 28, 1978, and which patent is incorporated herein by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 may be stretched and secured while the diaper 20 is in an uncontracted condition. Alternatively, the diaper 20 may be contracted, for example, by pleating, and the elastic members 44 secured and connected to the diaper 20 while the elastic members 44 are in their relaxed or unstretched condition.

In the embodiment illustrated in FIG. 1, the elastic members 44 extend essentially the entire length of the diaper 20 in the crotch region 26. Alternatively, the elastic members 44 may extend the entire length of the diaper 20, or any other length suitable to provide an elastically contractible line. The length of the elastic members 44 is dictated by the diaper design.

The elastic members 44 may take a multitude of configurations. For example, the width of the elastic members 44 may be varied from about 0.25 millimeters (0.01 inches) to about 25 millimeters (1.0 inch) or more; the elastic members 44 may comprise a single strand of elastic material or may comprise several parallel or non-parallel strands of elastic material; or the elastic members 44 may be rectangular or curvilinear. Still further, the elastic members 44 may be affixed to the diaper in any of several ways which are known in the art. For example, the elastic members 44 may be ultrasonically bonded, heat and pressure sealed into the diaper 20 using a variety of bonding patterns, or the elastic members 44 may simply be glued to the diaper 20.

The absorbent core 41 of the diaper 20 is positioned between the topsheet 38 and the backsheet 40. The absorbent core 41 may be manufactured in a wide variety of sizes and shapes (e.g., rectangular, hourglass, asymmetrical, etc.) and from a wide variety of materials. The total absorbent capacity of the absorbent core 41 should, however, be compatible with the design liquid loading for the intended use of the absorbent article or diaper. Further, the size and absorbent capacity of the absorbent core 41 may vary to accommodate wearers ranging from infants through adults. The absorbent core 41 preferably comprises the absorbent members of the present invention which comprise a mixture of fiber material and specific amounts of particles of the particulate, absorbent, polymeric compositions of the present invention containing interparticle crosslinked aggregates.

A preferred embodiment of the diaper 20 has a modified hourglass-shaped absorbent core 41. The absorbent core 41 is preferably an absorbent member 42 comprising a web or batt of airfelt, wood pulp fibers, and the particulate, absorbent, polymeric composition disposed therein.

Alternatively, the absorbent cores of the present invention may consist solely of the particulate, absorbent, polymeric compositions of the present invention, a combination of layers including the polymeric compositions of the present invention (including laminates as described herein) or any other absorbent core configurations as are known in the art. Examples of suitable absorbent core configurations are described, for example, in U.S. Pat. No. 3,670,731 issued to Harmon on Jun. 20, 1972; U.S. Pat. No. 3,669,114 issued to Morane on Jun. 15, 1972; U.S. Pat. No. 3,888,257 issued to Cook et al. on Jun. 10, 1975; U.S. Pat. No. 3,901,231 issued to Assarson et al. on Aug. 26, 1975; U.S. Pat. No. 4,102,340 issued to Mesek et al. on Jul. 25, 1978; and U.S. Pat. No. 4,500,315 issued to Pieniak et al. on Feb. 19, 1985. These patents are herein incorporated by reference.

An exemplary embodiment of an absorbent core 41 comprises a web comprising hydrophilic fiber material and the particulate, absorbent, polymeric composition of the present invention such as the absorbent member described in U.S. Pat. No. 4,610,678 entitled "High-Density Absorbent Structure" which issued to Paul T. Weisman and Stephen A. Goldman on Sep. 9, 1986, and which patent is incorporated herein by reference. An alternative embodiment of an absorbent core 41 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton, and Dale A. Gellert on Jun. 16, 1987, and which is incorporated herein by reference, having an asymmetric-shaped upper layer and a lower layer. A particularly preferred embodiment of the absorbent core 41 useful in the present invention is described in U.S. Pat. No. 4,834,735 entitled "High Density Absorbent Members Having Lower Density and Lower Basis Weight Acquisition Zones" issued to Miguel Alemany and Charles J. Berg on May 30, 1989, which discloses absorbent members having a storage zone and an acquisition zone having a lower average density and a lower average basis weight per unit area than the storage zone so that the acquisition zone may effectively and efficiently rapidly acquire discharged liquid. This patent is hereby incorporated herein by reference.

Figure 4:
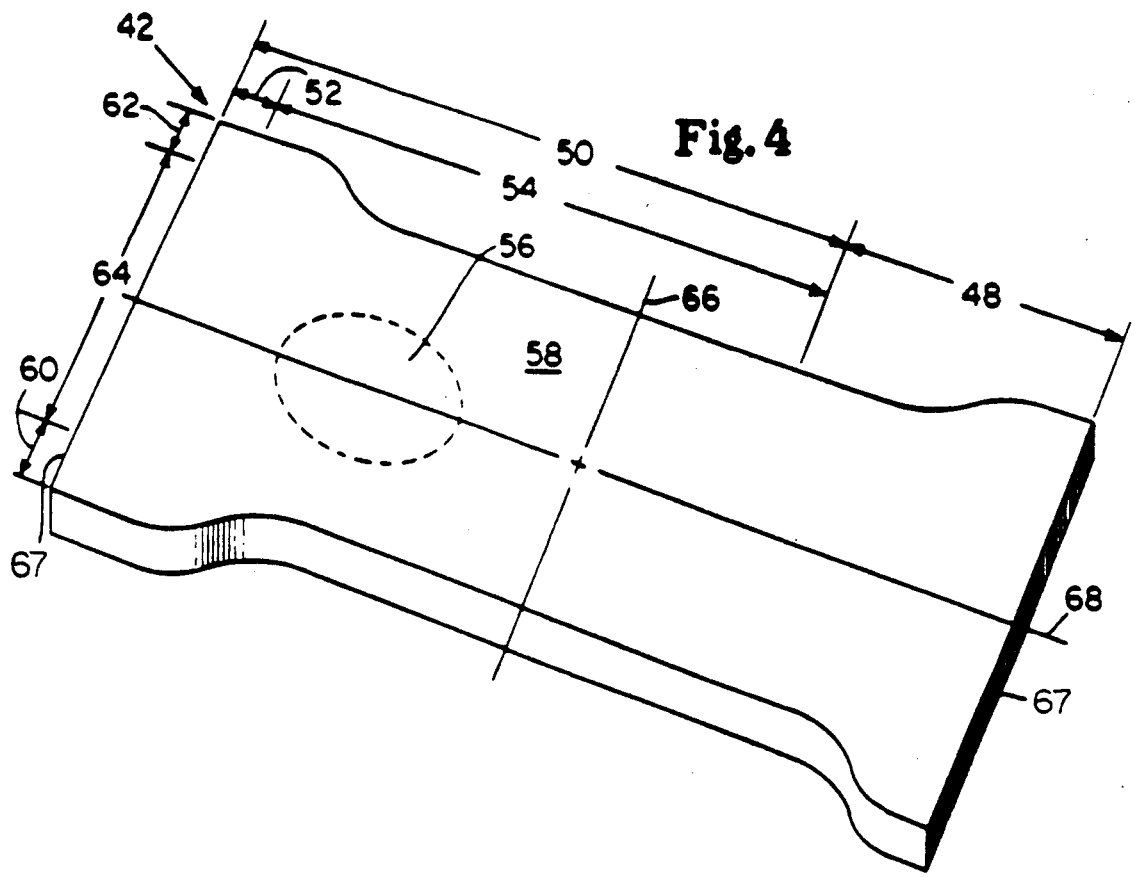
FIG. 4 is a perspective view of an absorbent member of the present invention used as an absorbent core in the disposable diaper shown in FIG. 1.

FIG. 4 is a perspective view of a preferred embodiment of the absorbent core 41 (absorbent member 42) of the present invention as described in the hereinbefore referenced U.S. Pat. No. 4,834,735. The absorbent member 42 is shown in FIG. 4 to comprise a back section 48 and a front section 50. The front section 50 is shown to have an end region 52 and a deposition region 54. The deposition region 54 comprises an acquisition zone 56 (shown by the dotted lines) and a storage zone 58. Further, the front section 50 is transversely divided into three regions comprising two transversely spaced ear regions 60 and 62 respectively, and a central region 64. The absorbent member 42 additionally has a transverse centerline which is designated 66 and a longitudinal centerline which is designated 68.

The absorbent member 42 has a back section 48 and a front section 50 that is contiguous with the back section 48. The back section 48 and the front section 50 of the absorbent member 42 extend respectively from the end edges 67 of the absorbent member 42 toward the transverse centerline 66, the front section 50 extending a distance from about one half to about three-fourths, preferably about two-thirds, of the length of the absorbent member 42. The front section 50 is preferably greater than one half of the total length of the absorbent member 42 so that it will encompass all of the area of typical liquid deposition of an absorbent member 42 when it is placed in a diaper or other absorbent article.

The front section 50 has an end region 52 and a deposition region 54. The end region 52 comprises that portion of the front section 50 extending from the respective end edge 70 of the absorbent member 42 toward the transverse centerline 66 a distance from about 2% to about 10%, preferably about 5%, of the length of the absorbent member 42. The deposition region 54 comprises that portion of the front section 50 that is contiguous with and positioned between the end region 52 and the back section 48 and encompasses the area of typical liquid deposition of the absorbent member 42.

The front section 50 further has two transversely spaced ear regions 60 and 62 respectively, and a central region 64 disposed intermediate the ear regions 60 and 62. The ear regions 60 and 62 comprise those portions which generally extend from the longitudinal edges 30 of the periphery 28 toward the longitudinal centerline a distance from about one-tenth to about one-third of the width of the absorbent member 42. Thus, the ear regions 60 and 62 are those portions that engage the side marginal portions of the wearer's waist and torso, whereas the central region 64 engages the medial portion of the wearer's waist and torso. The central region 64 thus defines the transverse area of typical liquid deposition.

The deposition region 54 comprises an acquisition zone 56 and a storage zone 58 in liquid communication with at least a portion of the lateral area of the acquisition zone 56. The acquisition zone 56 comprises portions of the deposition region 54 designated by the dotted lines in FIG. 4. The storage zone 58 generally comprises the remainder of the deposition region 54 and more preferably the remainder of the absorbent member 42.

The storage zone 58 is the relatively high capillarity (high density and high basis weight) portion of at least the deposition region 54. The primary functions of the storage zone 58 are to absorb discharged liquids that are either deposited directly onto the storage zone 58 or transferred to the storage zone 58 via the capillary force gradients established between the acquisition zone 56 and the storage zone 58, and to retain such liquids under the pressures encountered as a result of the wearer's movements. Preferably, the storage zone 58 consists essentially of the structure disclosed in the above-referenced U.S. Pat. No. 4,610,678 and the lower fluid storage layer disclosed in U.S. Pat. No. 4,673,402, both of which are incorporated herein by reference, although other high capillarity structures may also be used.

The storage zone 58 preferably has a relatively high density and a high basis weight per unit area in relation to the acquisition zone 56. The density and basis weight values of the storage zone 58 include the weight of the particles of the polymeric composition, such that the density and basis weight values will vary depending upon the amount of particles dispersed throughout the absorbent member 42.

Figure 2:
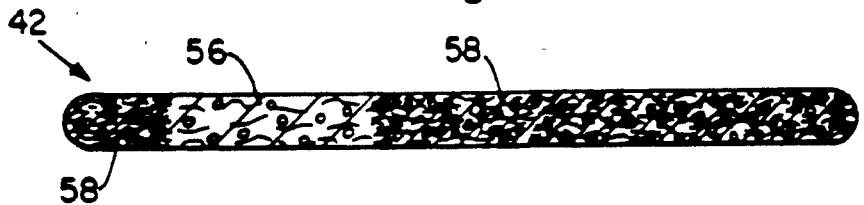
FIG. 2 is a longitudinal sectional view of only the absorbent core of the disposable diaper taken along sectional line 2—2 of FIG. 1.
Figure 3:
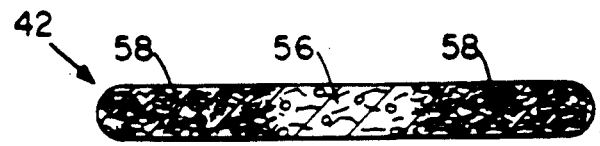
FIG. 3 is a transverse sectional view of only the absorbent core of the disposable diaper taken along sectional line 3—3 of FIG. 1.

While the storage zone 58 may take on a number of sizes and shapes, it is preferred that the storage zone 58 comprises the portion of at least the deposition region 54 wherein there is no acquisition zone 56. (i.e., The entire deposition region 54 comprises a storage zone 58 except for the acquisition zone 56.) While the back section 48 and the end region 52 need not comprise storage zones, in the particularly preferred embodiments of the absorbent member 42 as shown in FIGS. 2, 3, and 4, the entire absorbent member 42 except for the acquisition zone 56 consists of one or more storage zones 58. In addition, while the storage zone 58 need not completely laterally surround the acquisition zone 56 (i.e., it is in liquid communication with at least a portion of the lateral area of the acquisition zone 56), in preferred embodiments of the present invention, the storage zone 58 laterally surrounds the acquisition zone 56 so as to take full advantage of the capillarity difference between them.

The acquisition zone 56 has a relatively lower capillarity and thus preferably a lower average density and a lower average basis weight per unit area than the storage zone 58. The acquisition zone 56 serves to quickly collect and temporarily hold discharged liquids. Since such liquids are generally discharged in gushes, the acquisition zone 56 must be able to quickly acquire and transport liquid by wicking from the point of liquid contact to other parts of the absorbent member 42.

While portions of the acquisition zone 56 may be positioned in the back section 48 of the absorbent member 42, the acquisition zone 56 is preferably positioned generally in the front section 50 of the absorbent member 42 so that the acquisition zone 56 is positioned in the area of typical liquid deposition, i.e., the deposition region 54. Thus, the acquisition zone 56 is placed in the vicinity of the point of discharge of liquids so as to be capable of quickly acquiring such liquids at their contact zone.

The generally forward positioning of the acquisition zone 56 can be defined by specifying the percentage of the top surface area of the acquisition zone 56 which is found forward of particular points along the length of the absorbent member 42. While the positioning of the acquisition zone 56 can alternatively be defined with respect to the volume of the acquisition zone positioned forward of particular points, it has been found that the top surface area of the acquisition zone 56 is a more desirable definition because the top surface area actually defines the initial area available for liquid acquisition. In addition, since the thickness of the absorbent member 42 is preferably uniform in the deposition region 54 and the acquisition zone 56 has a generally rectangular cross-sectional area, the top surface area definition is equal to a volumetric definition in a preferred embodiment. Thus, the positioning of the acquisition zone 56 will be referenced throughout the specification as related to its top surface area. (i.e., The percentage of the top surface area of the acquisition zone positioned in a given area.)

Thus, in accordance with the present invention, at least a portion of the acquisition zone 56 must be placed in the deposition region 54, even though the remaining portion may be positioned anywhere in the absorbent member 42 including the back section 48 and the end regions 52. (It being understood that if plural acquisition zones are utilized, at least a portion of one of the acquisition zones must be positioned in the deposition region 54.) However, the acquisition zone 56 is preferably positioned relative to the absorbent member 42 such that the top surface area of the acquisition zone 56 is completely positioned within the front section 50 of the absorbent member 42. More preferably, the acquisition zone 56 is positioned relative to the absorbent member 42 such that the top surface area of the acquisition zone 56 is completely positioned within the deposition region 54 of the absorbent member 42. Even more preferably, at least 30% of the top surface area of the acquisition zone 56 is positioned in the front half of the front section (approximately the front ⅓ of the overall absorbent member 42) of the absorbent member 42.

The acquisition zone 56 can be of any desired shape consistent with the absorbency requirements of the absorbent member 42 or diaper 20 including, for example, circular, rectangular, triangular, trapezoidal, oblong, hourglass-shaped, funnel-shaped, dog-bone-shaped, fox-shaped or oval. Preferred shapes of the acquisition zone 56 are those that increase the perimeter of the interface between the acquisition zone 56 and the storage zone 58 so that the relative capillarity difference between the zones are fully utilized. In the embodiment shown in FIGS. 1–4, the acquisition zone is oval shaped having a top surface area of about 45 cm$^2$ (about 7 in$^2$).

In order to maintain a certain minimal absorbency level in the front section 50 of the absorbent member 42, the top surface area or volume of the storage zone 58 must comprise some minimal amount of the top surface area or volume of the front section 50. Thus, it has been found that the acquisition zone 56 should preferably comprise less than the entire top surface area and/or volume of the front section 50 of the absorbent member 42. (Since in a preferred embodiment the acquisition zone 56 is of generally uniform thickness and cross-sectional area, volume can be interchanged with top surface area as a definitional point.) The top surface area of the portion of the acquisition zone 56 positioned in the front section 50 of the absorbent member 42 preferably comprises less than about 50% of the top surface area of the front section 50. More preferably, the top surface area of the acquisition zone 56 comprises less than about 35% of the top surface area of the front section 50 of the absorbent member 42, with less than about 20% being especially preferred. In addition, the top surface area of the acquisition zone 56 preferably comprises less than about 50% of the top surface area of the deposition region 54, more preferably less than about 35%, and most preferably less than about 20%.

The acquisition zone 56 may also have a number of different cross-sectional areas and configurations including those wherein the area of portions of the acquisition zone 56 is less or greater than its top surface area (i.e., The acquisition zone 56 is smaller or wider below the top surface of the absorbent member 42.) For example, the acquisition zone 56 may have conical, trapezoidal, T-shaped or rectangular cross-sectional areas. As shown in FIGS. 2 and 3, the acquisition zone 56 preferably has a rectangular cross-sectional area so as to provide a uniform acquisition zone 56.

In addition, the acquisition zone 56 need not comprise the entire thickness of the absorbent member 42, it may extend through only a fraction of its total thickness. The acquisition zone 56 may also have a different thickness than the laterally surrounding storage zone 58. However, in a preferred embodiment as shown in FIGS. 2 and 3, the acquisition zone 56 preferably extends through the entire thickness of the absorbent member 42 and has a thickness equal to the thickness of the surrounding storage zone 58 in the deposition region 54.

While the acquisition zone 56 may be transversely positioned anywhere along the absorbent member 42, it has been found that the acquisition zone 56 functions the most efficiently when it is transversely centered within the front section 50 or the deposition region 54 of the absorbent member 42. Thus, the acquisition zone 56 is preferably centered about the longitudinal centerline 68 of the absorbent member 42. More preferably, the acquisition zone 56 is transversely positioned only in the central region 64 of the front section 50 or deposition region of the absorbent member 42 such that none of the acquisition zone 56 is located in the ear regions 60 and 62.

Such an absorbent member 42 is preferably made by airlaying a thickness profiled absorbent member-preform and then calendering the absorbent member 42 in a fixed-gap calender roll to effect densifying of the absorbent member 42. The thickness profiled absorbent member 42 initially has areas of higher basis weight which define the storage zone 58 and of lower basis weight which define the acquisition zone 56. The absorbent member 42 is then calendered preferably to at least a uniform thickness in the deposition region. Thus, a lower average density and a lower average basis weight per unit area acquisition zone 56 is created relative to the higher average density and higher average basis weight storage zone 58. Additionally, the particulate, absorbent, polymeric composition is added to an air-entrained stream of fibers prior to their deposition onto the preform to affect uniform distribution of the polymeric composition throughout the preformed absorbent member 42.

Figure 6:
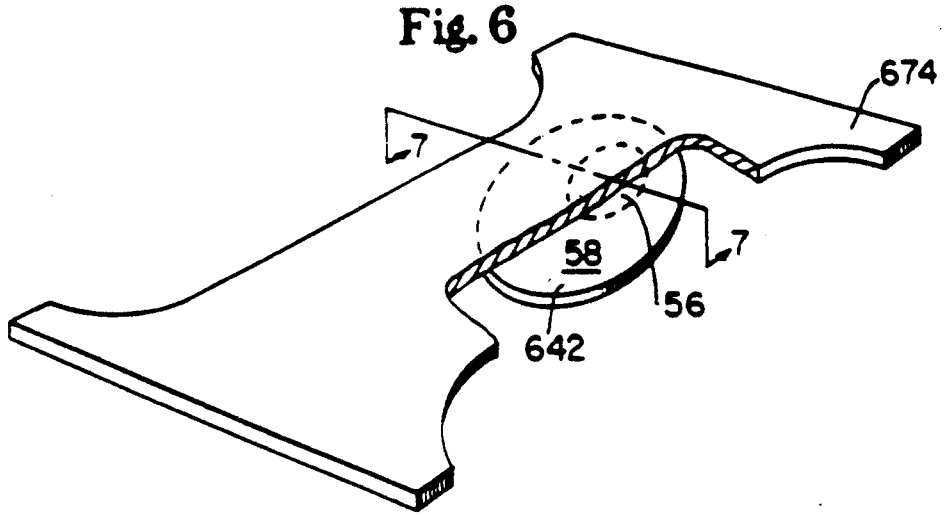
FIG. 6 is a perspective view of an alternative embodiment dual-layer absorbent member of the present invention.
Figure 7:
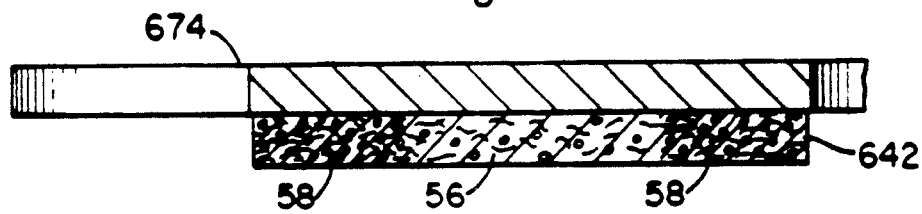
FIG. 7 is a sectional view of the dual-layer absorbent member of FIG. 6 taken along sectional line 7—7 of FIG. 6.

FIGS. 6 and 7 show a further alternative embodiment of an absorbent core of the present invention. An absorbent acquisition layer 674 is positioned over the absorbent member 642 to form a dual-layer absorbent core. An example of a similar dual-layer absorbent core is discussed in more detail in the above-referenced U.S. Pat. No. 4,673,402, which is incorporated herein by reference.

This absorbent acquisition layer 674 serves to quickly collect and temporarily hold discharged liquids and to transport such liquids by wicking from the point of initial contact to other parts of the absorbent acquisition layer 674. Since the primary function of the absorbent acquisition layer 674 is to receive liquids passing through the topsheet 38 and to transport such liquids to other areas of the absorbent acquisition layer 674 and eventually onto the absorbent member 642, the absorbent acquisition layer 674 can be substantially free of the polymeric composition. The absorbent acquisition layer 674 preferably consists essentially of hydrophilic fibrous material. Alternatively, the absorbent acquisition layer 674 can contain specific amounts of the polymeric composition. Thus, the absorbent acquisition layer 674, for example, can contain up to about 50% by its weight of the polymeric composition. In the most preferred embodiments, the absorbent acquisition core contains from 0% to about 8% by its weight of the polymeric composition. In alternatively preferred embodiments, the absorbent acquisition layer 674 comprises chemically stiffened cellulosic fibers as previously discussed herein.

The absorbent acquisition layer 674 in the unfolded configuration can be of any desired shape, for example, rectangular, oval, oblong, asymmetric or hourglass-shaped. The shape of the absorbent acquisition layer 674 may define the general shape of the resulting diaper 20. In preferred embodiments of the present invention as shown in FIG. 6, the absorbent acquisition layer 674 will be hourglass-shaped.

The absorbent member 642 of the present invention need not be the same size as the absorbent acquisition layer 674 and can, in fact, have a top surface area which is substantially smaller or larger than the top surface area of the absorbent acquisition layer 674. As shown in FIG. 6, the absorbent member 642 is smaller than the absorbent acquisition layer 674 and has a top surface area from about 0.25 to about 1.0 times that of the absorbent acquisition layer 674. Most preferably, the top surface area of the absorbent member 642 will be only from about 0.25 to about 0.75, and most preferably from about 0.3 to about 0.5, times that of the absorbent acquisition layer 674. In an alternative embodiment, the absorbent acquisition layer 674 is smaller than the absorbent member 642 and has a top surface area from about 0.25 to about 1.0 times, more preferably from about 0.3 to about 0.95 times, that of the absorbent member 642. In this alternative embodiment, the absorbent acquisition layer 642 preferably comprises chemically stiffened cellulosic fibers.

The absorbent member 642 is preferably placed in a specific positional relationship with respect to the backsheet 40 and/or the absorbent acquisition layer 674 in the diaper or other absorbent article. More particularly, the absorbent member 642 is positioned generally toward the front of the diaper so that the polymeric composition is most effectively located to acquire and hold discharged liquids from the absorbent acquisition layer 674.

The forward positioning of the absorbent member 642 can be defined by specifying the percent of total polymeric composition which is found forward of particular points along the length of the diaper or other absorbent article. Thus, in accordance with the present invention, the absorbent member 642 is positioned relative to the backsheet and/or the absorbent acquisition layer 674 such that (1) at least about —75% of the total polymeric composition in the absorbent member 642 is found within the front two-thirds portion of the diaper or other absorbent article, and (2) at least about 55% of the total polymeric composition in the absorbent member 642 is found within the front half portion of the diaper or other absorbent article. More preferably, the absorbent member 642 is positioned relative to the backsheet 38 and/or the absorbent acquisition layer 674 such that at least about 90% of the total polymeric composition in the absorbent member 642 is found in the front two-thirds portion and at least about 60% of the total polymeric composition is found in the front half portion of the diaper or other absorbent article. (For purposes of the present invention, "portions" of the diaper or other absorbent article can be defined by reference to the top surface area of the unfolded diaper 20 or absorbent article found in front of a given point on the line which defines the length of the diaper 20 or absorbent article.)

The absorbent member 642 of the dual-layer absorbent core can be of any desired shape consistent with comfortable fit including, for example, circular, rectangular, trapezoidal, oblong, hourglass-shaped, dog-bone-shaped, or oval. If desired, the absorbent member 642 can be wrapped in a high wet strength envelope web such as tissue paper or a synthetic fine pore (e.g., non-woven) material to minimize the potential for particles of the polymeric composition to migrate out of the absorbent member 642. Another objective of such overwrapping is to desirably increase the in-use integrity of the dual-layer absorbent core. Such a web can, in fact, be glued to the absorbent member 642. Suitable means for carrying out this gluing operation include the glue spraying procedure described in U.S. Pat. No. 4,573,986 issued to Minetola and Tucker, on Mar. 4, 1986, which patent is incorporated herein by reference.

In preferred embodiments, as shown in FIG. 6, the absorbent member 642 of the dual-layer absorbent core will be oblong. In especially preferred embodiments, an oblong absorbent member 642 overwrapped with spray-glued tissue will be employed.

Figure 8:
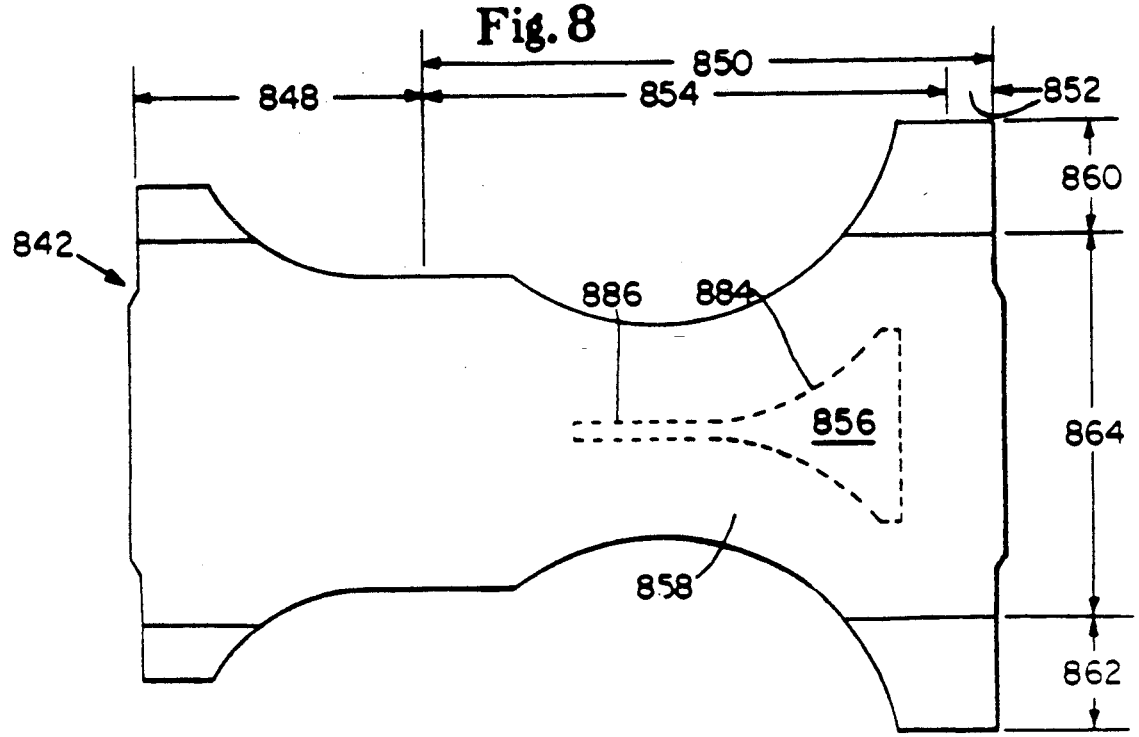
FIG. 8 is a plan view of a further alternative embodiment of an absorbent member of the present invention.

FIG. 8 shows a still further alternative embodiment of an absorbent core comprising absorbent member 842 of the present invention. The absorbent member 842 has an asymmetric shape (i.e., the absorbent member 842 is not symmetrical about its transverse centerline). In addition, the density and basis weight values of the ear regions 860 and 862 and the back section 848 are different from the storage zone 858 positioned in the central region 864 by virtue of the method by which the absorbent member 842 is formed. The ear regions 860 and 862 and the back section 848 are preferably formed with a lesser basis weight than the storage zone 858 of the central region 864 because the extra material would, in this embodiment, provide no significant incremental benefits in leakage protection such that the cost of such absorbent member 842 is lowered. The absorbent member 842 is calendered to a uniform thickness; the storage zone 858 of the central region 864, therefore, having a greater average density than the back section 848 and the ear regions 860 and 862. (It should be understood that all or portions of the back section 848 and the ear regions 860 and 862 may alternatively be calendered to a lesser thickness than the central region 864 such that they have about an equal or a greater average density than the storage zone 858.) Further, as shown in FIG. 8, the back section 848 preferably contains ears, although it need not contain such ears.

The acquisition zone 856 of the absorbent member 842 has a funnel shape. The funnel shape is defined by a generally triangular portion 884 in combination with a stem or rectangular portion 886. The triangular portion 884 is especially effective in absorbing liquids discharged by a male wearer, while the stem portion 886 is effective for a female wearer. In order to resist closure of the stem portion 884 of the acquisition zone 856 during manufacture or use, the stem portion 884 should have a minimum width, preferably at least about 154 inch for the fibrous material preferably used herein. The shape of the acquisition zone 856 may also vary according to the type of wearer contemplated, such as preferably only a triangular portion 884 for a male wearer.

Figure 9:
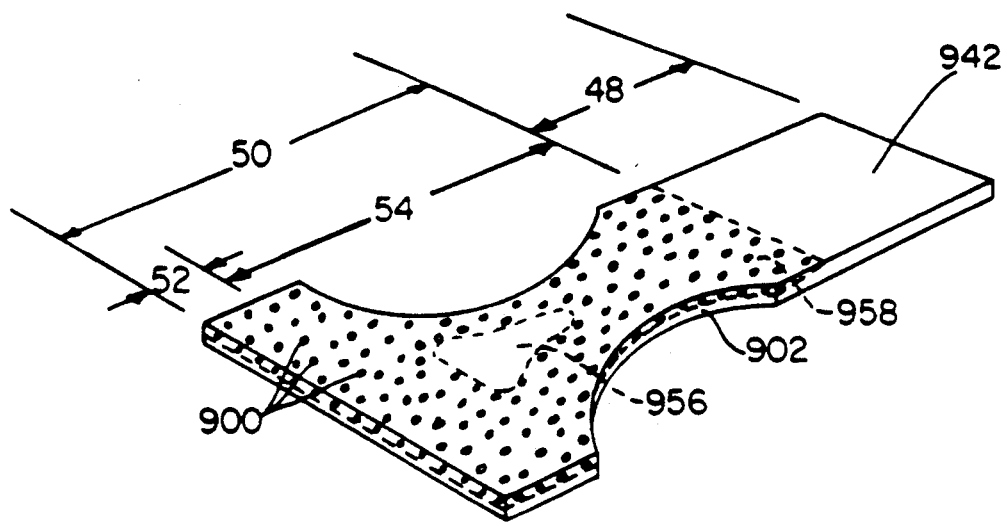
FIG. 9 is a perspective view of another alternative embodiment of an absorbent member of the present invention.

FIG. 9 shows a further alternative embodiment of the present invention in which the absorbent core may comprise absorbent member 942 comprising a stratified matrix of fiber material and a mixture of fiber material and particles 900 of the polymeric composition of the present invention. The absorbent member 942 thus comprises a storage zone 958 (designated by the dotted lines), and a dusting layer 902 (acquisition/distribution layer). The storage zone 958 is preferably positioned only in the front section 850 of the absorbent member 942 such that the back section 48 does not comprise a storage zone 958 (i.e., the back section 48 does not comprise a mixture of fibrous material and the polymeric composition). This configuration both saves on material costs and provides a leakage benefit at the end of the absorbent member 942. In addition, both the storage zone 958 and the acquisition zone 956 do not comprise the entire thickness of the absorbent member 942, but extend only through a fraction (preferably between about 25% and about 95%, more preferably between about 75% and about 95%) of the total thickness of the absorbent member 942. Thus, the dusting layer 902 is preferably relatively thinner in thickness than the acquisition zone 956 and the storage zone 958 of the absorbent member 942 and is formed from at least the portion of the thickness of the absorbent member 942 not comprising the acquisition zone 956 and the storage zone 958; more preferably, the dusting layer 902 also being formed from the back section 48 of the absorbent member 942. In the embodiment illustrated, both the acquisition zone 956 and the dusting layer 902 preferably consist essentially of hydrophilic fiber material that has limited quantities (from about 0% to about 2%) of the polymeric composition dispersed therein. Further, the acquisition zone 956 and the dusting layer 902 are made of the same materials and have the same density and basis weight so that the absorbent member 942 has, in essence, an overall acquisition zone surrounding the storage zone 958.

Body liquids that are deposited onto the acquisition zone 956 will be quickly acquired into the absorbent member 942 where they will be either transported into the storage zone 958 by the capillary gradient between the storage zone 958 and the acquisition zone 956 along their interface, or wicked or pulled by gravity into the dusting layer 902 whereupon the liquids will be rapidly transported by wicking from the point of initial contact at the acquisition zone 956 to other parts of the dusting layer 902 where the capillary difference between the dusting layer 902 and the storage zone 958 will cause the liquid to be transported into the storage zone 958. Thus, a greater area of capillary gradients exists between the storage zone 958 and other portions of the absorbent member 942 such that the storage zone 958 and, more particularly, the particles 900 of the polymeric composition are more efficiently used. Thus, while the acquisition zone 956 and the dusting layer 902 may have different characteristics and constructions such as being made of different materials, having different densities, or having particles of the polymeric composition dispersed in either, it is preferred that the acquisition zone 956 and the dusting layer 902 consist of the same material, have the same density, and be essentially devoid of particles of the polymeric composition so that the liquids may rapidly wick into and through the absorbent member 942.

The absorbent member 942 of this alternative embodiment is preferably manufactured by the methods and apparatus disclosed in U.S. Pat. No. 4,888,231, entitled "Absorbent Cores Having a Dusting Layer" which issued to John J. Angstadt on Dec. 19, 1989; which patent is incorporated herein by reference. Thus, the absorbent member 942 is preferably made by airlaying a layer of only fibrous material onto a profiled absorbent member-preform to form what will be the dusting layer 902 and the acquisition zone 956. The storage zone 956 is then airlaid over the dusting layer and the absorbent member is calendered to a uniform thickness.

Figure 10:
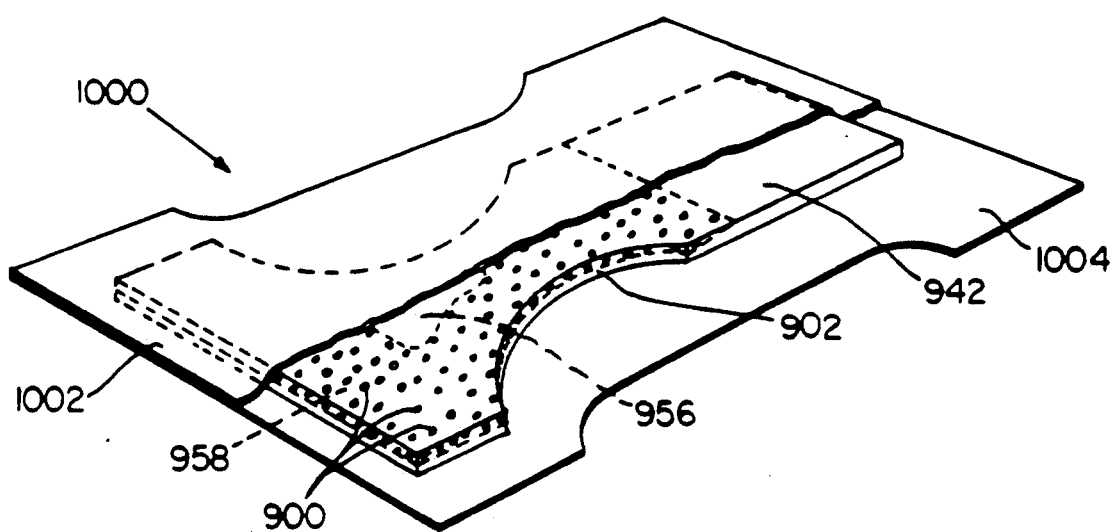
FIG. 10 is a cut-away perspective view of a disposable diaper embodiment of the present invention containing the absorbent member shown in FIG. 9.

FIG. 10 shows a perspective view of an alternative diaper embodiment of the present invention in which the absorbent member 942 of FIG. 9 is encased between a topsheet 1002 and a backsheet 1004 to form the disposable diaper 1000. The absorbent member 942 is preferably positioned such that the dusting layer 902 is positioned adjacent the backsheet 1004 so that the absorbent member 942 may function as hereinbefore described. Although not preferred, the storage zone 958 may alternatively be positioned adjacent the backsheet 1004 so that the dusting layer 902 acts as a fluid distribution/acquisition layer and the storage zone 958 acts as a lower fluid storage layer such as the structure described in the hereinbefore referenced U.S. Pat. No. 4,673,402.

Figure 11:
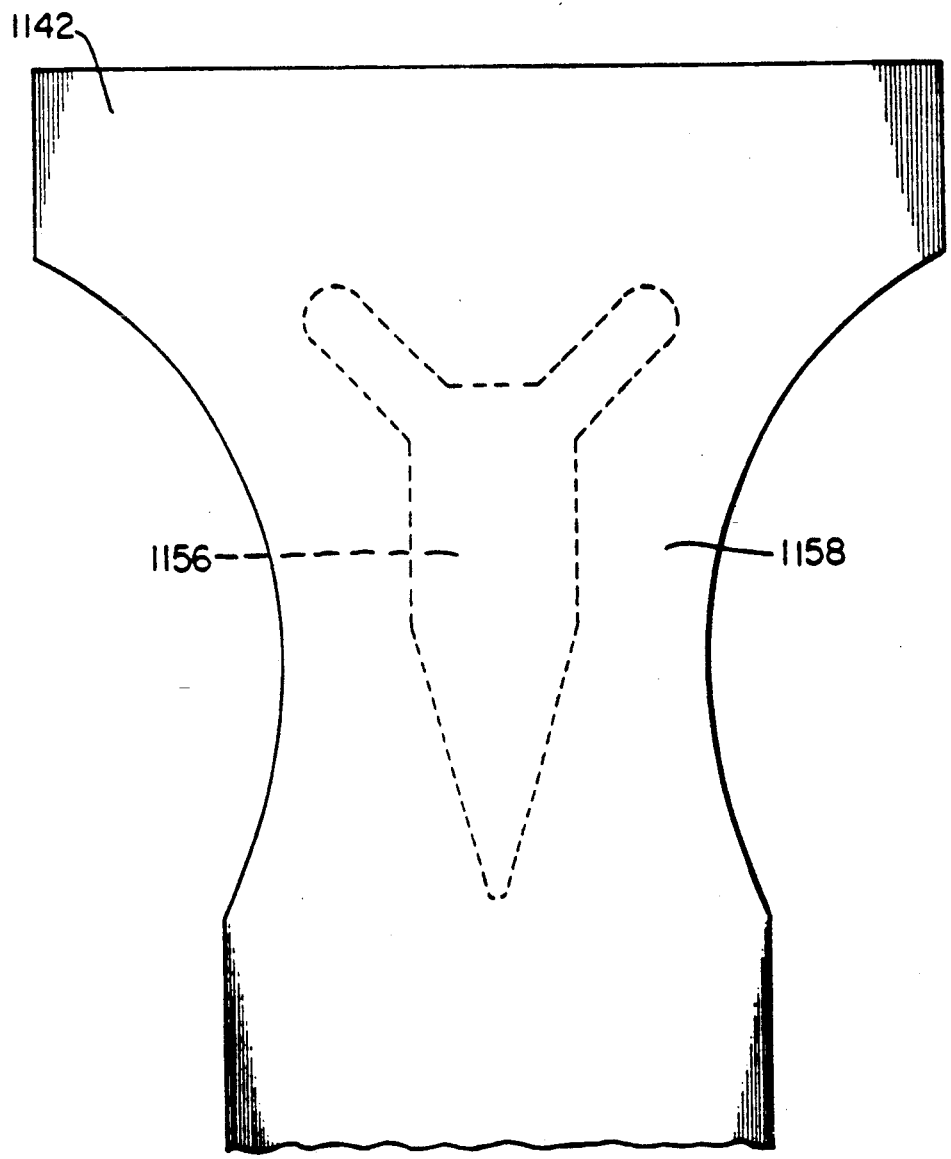
FIG. 11 is a top view of a portion of an absorbent member according to the present invention showing a preferred shape for the acquisition zone.

FIG. 11 shows a further alternative embodiment of the present invention wherein the shape of the acquisition zone 1156 (shown by the dotted lines) is "fox-shaped." (So called because it resembles the front profile of a fox's head.) As previously discussed, a triangular acquisition zone has been found to be especially effective for male wearers. However, such an acquisition zone does not perform as well for female wearers. It has been found that an optimized shaped for an acquisition zone for females is the fox-shape shown in FIG. 11. The fox-shape increases the perimeter of the interface between the acquisition zone 1156 and the storage zone 1158. In addition, the fox-shape is positioned farther from the front end of the absorbent member 1142 than the triangular acquisition zone utilized for males so as to be placed nearest the point of discharge because of the anatomical difference between males and females. Thus, the fox-shaped acquisition zone 1156 enhances fluid distribution for female wearers.

Yet another alternative to the embodiments of the above absorbent members comprises varying the pore size of the fibers without necessarily varying the density of the fibers to form an acquisition zone and a storage zone. For example, fine fiber dimensions of hardwood fluff can be utilized to advantage by substituting at least about 50%, and preferably about 80% to 100%, hardwood fluff fibers of approximately the same density as lower density softwood fluff fibers for the softwood fibers in the storage zone. This can be done because the hardwood fluff has a smaller pore size than the softwood fluff material. As result, a capillarity difference will still be obtained within the scope of the invention, even if the density of each zone is the same. Thus, for example, an absorbent member can be obtained from using a predominately softwood pulp with a fine pore structure to define the acquisition zone and a predominately hardwood fluff pulp to define the storage zone.

In use, the diaper 20 is applied to a wearer by positioning the back waistband region 24 under the wearer's back, and drawing the remainder of the diaper 20 between the wearer's legs so that the front waistband region 22 is positioned across the front of the wearer. The tape-tab fasteners 46 are then secured preferably to outwardly facing areas of the diaper 20.

Because the particulate, absorbent, polymeric compositions, and thus the absorbent members, of the present invention have a high absorbent capacity for menstrual fluids as well as for urine, such structures, even though defined in terms of capacity for Synthetic Urine, are also quite suitable for use in sanitary napkins.

Figure 17:
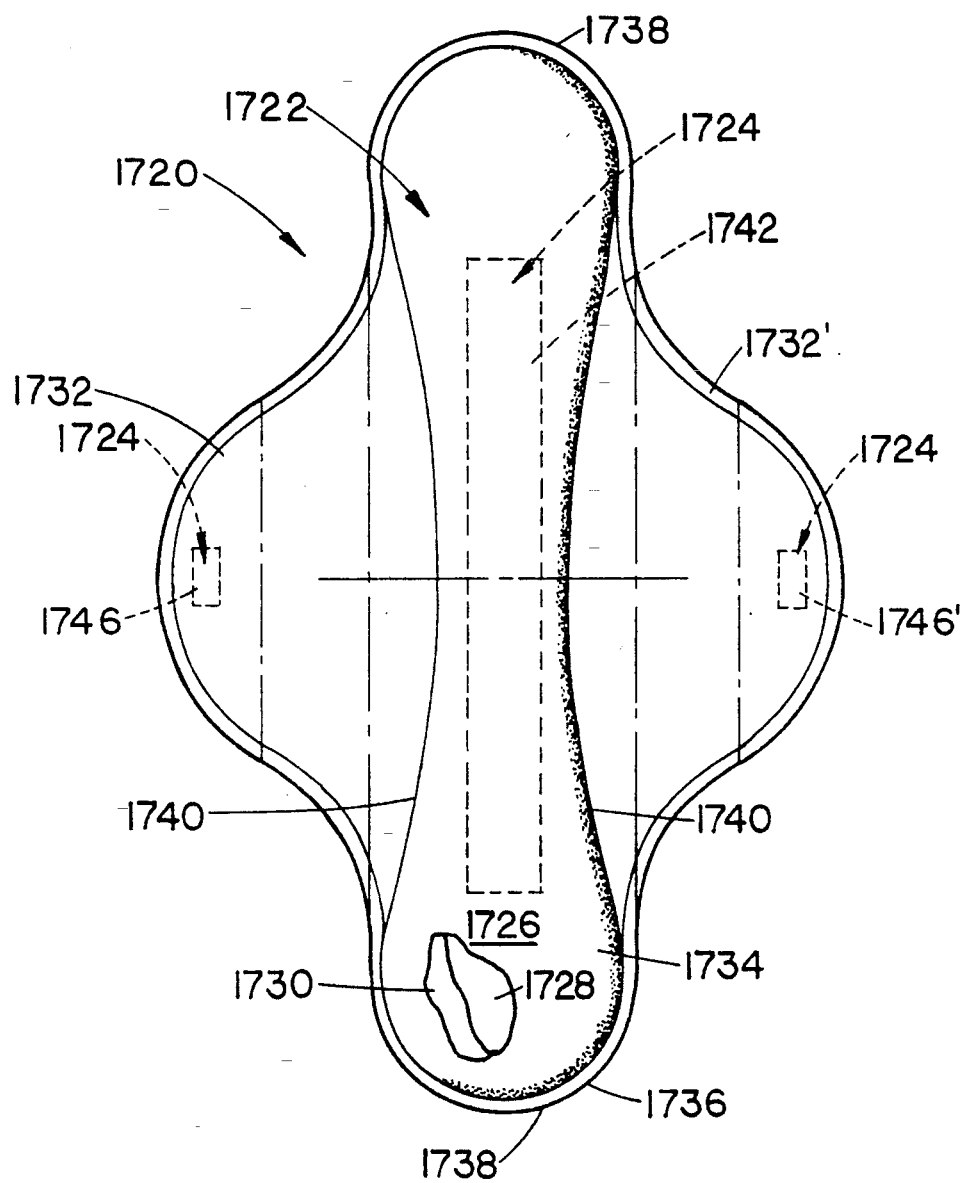
FIG. 17 is a partially cut-away plan view of a sanitary napkin embodiment of the present invention.

FIG. 17 shows an alternative embodiment of the present invention wherein the disposable absorbent article is a sanitary napkin 1720 designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is very readily adapted are shown in U.S. Pat. No. 4,687,478 entitled "Shaped Sanitary Napkin With Flaps" which issued to Kees J. Van Tilburg on Aug. 18, 1987; U.S. Pat. No. 4,589,876 entitled "Sanitary Napkin" which issued to Kees J. Van Tilburg on May 20, 1986; U.S. Pat. No. 4,681,578 entitled "Pantiliner with Ventilation Areas" which issued to Arthur B. Anderson and Sherry L. Brandt on Jul. 21, 1987; and U.S. Pat. No. 4,690,680 entitled "Adhesive Attachment Means for Absorbent Articles" which issued to Maureen L. Higgins on Sep. 1, 1987. Each of these patents are herein incorporated by reference. It will be apparent from the following description that the particulate, absorbent, polymeric compositions and the absorbent members described herein may be used as the absorbent core of such sanitary napkins. On the other hand, it will be understood the present invention is not limited to any specific sanitary napkin structure or configuration.

FIG. 17 is a plan view of a sanitary napkin 1720 embodying the present invention prior to it being placed in the undergarment of the wearer. As can be shown in FIG. 17, a preferred sanitary napkin construction comprises a liquid pervious topsheet 1726, an absorbent core 1728, a liquid impervious backsheet 1730, and a fastening system 1724 for securing the sanitary napkin 1720 to the undergarment of the wearer. While the topsheet 1726, the absorbent core 1728, and the backsheet 1730 may be assembled in a variety of well-known configurations, a preferred sanitary napkin configuration is shown and described generally in the above-referenced U.S. Pat. No. 4,687,478, wherein the sanitary napkin 1720 additionally has flaps 1732 and 1732'.

FIG. 17 shows a preferred embodiment of the sanitary napkin 1720 in which the topsheet 1726 and the backsheet 1730 are coextensive and have length and width dimensions generally larger than those of the absorbent core 1728 to form the flaps 1732 and 1732'. The topsheet 1726 is joined with and superposed on the backsheet 1730 to form the periphery of the sanitary napkin 1720. The sanitary napkin 1720 has an inside surface 1734 and an outside surface 1736. In general, the outside surface 1736 extends from one end edge 1738 to the other end edge 1738 and from one longitudinal edge 1740 to the other longitudinal edge 1740 and is the surface farthest from the wearer during use of the sanitary napkin 1720 and is designed to fit adjacent the undergarment of the wearer. When a backsheet 1730 is used, it typically forms the outside surface 736. The inside surface 1734 is that surface opposite the outside surface 736 and in the embodiment shown is typically formed by the topsheet 1726. In general, the inside surface 1734 is that surface coextensive with the outside surface 1736 and which is for the greater part in contact with the wearer when the sanitary napkin 1720 is worn.

In the preferred embodiment of the sanitary napkin 1720 as shown in FIG. 17, the fastening system 1724 comprises an attachment member 1742 positioned on the outside surface 1736 of the sanitary napkin 1720 and a release liner (not shown) as is known in the art releasably attached to the adhesive of the attachment member 1742.

Since a preferred embodiment of the sanitary napkin 1720 of the present invention comprises flaps 1732 and 1732', a flap attachment member 1746 is also provided on one or both of the flaps 1732 and 1732' to maintain the flaps 1732 and 1732' in position after the flaps 1732 and 1732' have been wrapped around the edge of the crotch portion of the undergarment. A release liner (not shown) is also positioned over each of the flap attachment members 1746 to protect the adhesive until the sanitary napkin 1720 is used, the release liner being removed and the flap being wrapped around the edge of the crotch portion of the undergarment.

The topsheet 1726 may comprise any of the topsheet materials discussed with respect to diapers. In a preferred embodiment, the topsheet 1726 preferably comprises a formed thermoplastic film such as is described in U.S. Pat. No. 4,342,314 entitled "Resilient Plastic Web Exhibiting Fiber-Like Properties" which issued to Clifford J. Radel and Hugh A. Thompson on Aug. 3, 1982; and U.S. Pat. No. 4,463,045 entitled "Macroscopically Expanded Three-Dimensional Plastic Web Exhibiting Non-Glossy Visible Surface and Cloth-Like Tactile Impression" which issued to Nicholas A. Ahr, William I. Mullane, Jr., and William R. Ouellette on Jul. 31, 1984; which patents are incorporated herein by reference.

The backsheet 1730 may comprise any of the backsheet materials discussed with respect to diapers. The backsheet preferably comprises a polyethylene film.

The absorbent core 1728 is positioned between the topsheet 1726 and the backsheet 1730 and may comprise any of the absorbent members of the present invention or of only the particulate, absorbent, polymeric compositions of the present invention. In an alternative embodiment of the sanitary napkin 1726, the absorbent core 728 comprises a laminate (a layered absorbent member) as described herein.

In use, the sanitary napkin 1720 is secured on the inside of the crotch portion of an undergarment with the pressure-sensitive adhesive fastener side of the sanitary napkin 1720 toward the crotch portion of the undergarment. Thus, the undergarment serves as the landing member for the fastening system 1724. The release liner is removed from the attachment member 1742 and the sanitary napkin 1720 is secured in position by pressing the exposed pressure-sensitive adhesive fastener 1742 firmly against the crotch material of the undergarment.

SYNTHETIC URINE

The specific synthetic urine used in the test methods of the present invention is referred to herein as "Synthetic Urine". The Synthetic Urine is commonly known as Jayco SynUrine and is available from Jayco Pharmaceuticals Company of Camp Hill, Pa. The formula for the Synthetic Urine is: 2.0 g/l of KCl; 2.0 g/l of $Na_2SO_4$; 0.85 g/l of $(NH_4)H_2PO_4$; 0.15 g/l $(NH_4)_2HPO_4$; 0.19 g/l of $CaCl_2$; and 0.23 g/l of $MgCl_2$. All of the chemicals are of reagent grade. The pH of the Synthetic Urine is in the range of 6.0 to 6.4.

TEST METHODS

A. Riffling and Sieving of Samples

In order to test representative samples of the polymeric compositions in the tests described hereinafter, specific "cuts" of the samples are produced. The specific cut chosen for the tests herein is a sample of from about 300 microns (a standard #50 sieve) to about 850 microns (a standard #20 sieve). Thus, the samples to be tested herein are designated a 20/50 cut. In order to obtain the riffled and sieved 20/50 cut, a sample or plurality of particles is riffled and then sieved through a set number of screens of diminishing screen opening size.

40 grams of a representative bulk sample of the polymeric composition is riffled into eight approximately equal fractions. The sample is riffled, following the manufacturer's instructions, with a Rotary Microriffler Model RR-4 obtainable from the Quantachrome Co. of Syosset, N.Y. One of these fractions is then transferred onto a sieve stack: the stack containing, from the top, a standard #20 sieve (850 microns), a standard #50 sieve (300 microns), and a sieve pan. The riffled fraction is sieved, following the manufacturer's instructions, with a Vibratory 3-Inch Sieve Shaker Model SS-5. The Sieve Shaker and the standard #20 sieve (300 micrometers), the standard #50 sieve (850 microns), and the sieve pan are obtainable from Gilson Company, Inc. of Worthington, Ohio. The riffled fraction is shaken for 3 minutes at approximately 2100 vibrations per minute ("6" on the instrument dial) to obtain a sample in the particle size range of 300 to 850 microns, that is, a sample consisting of particles which passes through a 20 mesh sieve (#20 sieve) and are retained on a 50 mesh sieve (#50 sieve), hereinafter referred to as a 20/50 cut sample.

B. Swelling Rate

A 20/50 cut sample of the polymeric composition is placed into a test tube, a specific amount of Synthetic Urine is added to the sample, and the time required for the sample to absorb the Synthetic Urine is measured. The rate of fluid uptake of the sample determines the swelling rate. The swelling rate measures the average rate of fluid uptake of a 20/50 cut sample to a 28 gram per gram loading in the presence of potential gel blocking conditions. As the gel mass expands upward in the fluid in the tube, the gel "bed height" increases. For polymeric compositions especially prone to gel blocking, it reaches a point at which the permeability of the gel bed limits the swelling of the interior gel particles. That is, the speed at which the fluid can penetrate and move through the bed is less than the speed at which the fluid can be diffused into the particles. For polymeric compositions with minimal gel blocking properties, this method will yield results virtually unaffected by bed properties.

The following procedure is conducted under standard laboratory conditions at 23° C. (73° F.) and 50% relative humidity. Using a standard three decimal place balance, 0.358 grams plus or minus 0.001 grams of a 20/50 cut sample of the polymeric composition is weighed out and placed in the bottom of a standard 16 mm diameter test tube as obtainable from Fisher Scientific Co. of Pittsburgh, Pa. 10.0 ml of Synthetic Urine is added to the vertically supported test tube, while at the same time activating a stopwatch. The stopwatch is stopped at the moment when the rising gel mass of the swelling polymeric composition reaches the bottom of the meniscus of the Synthetic Urine in the test tube. The swelling rate (sr) of the polymeric composition is calculated as follows: sr=(the amount of Synthetic Urine per gram of polymeric composition added to the sample, in this case the value is 28) divided by (time elapsed in seconds). The Swelling Rate value for use herein is the average swelling rate of three samples.

It should be noted that the Swelling Rate of polymeric compositions of various loadings (not just 28× loadings) can be determined by varying the amount of Synthetic Urine added to the 20/50 cut sample. For example, a "15×" Swelling Rate may be calculated by adding 5.36 ml of Synthetic Urine to a 0.358 gram sample.

C. Gel Expansion Pressure

A 20/50 cut sample of the polymeric composition is placed into a special gel expansion pressure apparatus, as described hereinafter, and is contacted with a specific amount of Synthetic Urine. The net force exerted by the swollen gel mass of the sample is measured by the apparatus which is then converted into the Gel Expansion Pressure.

Figure 18:
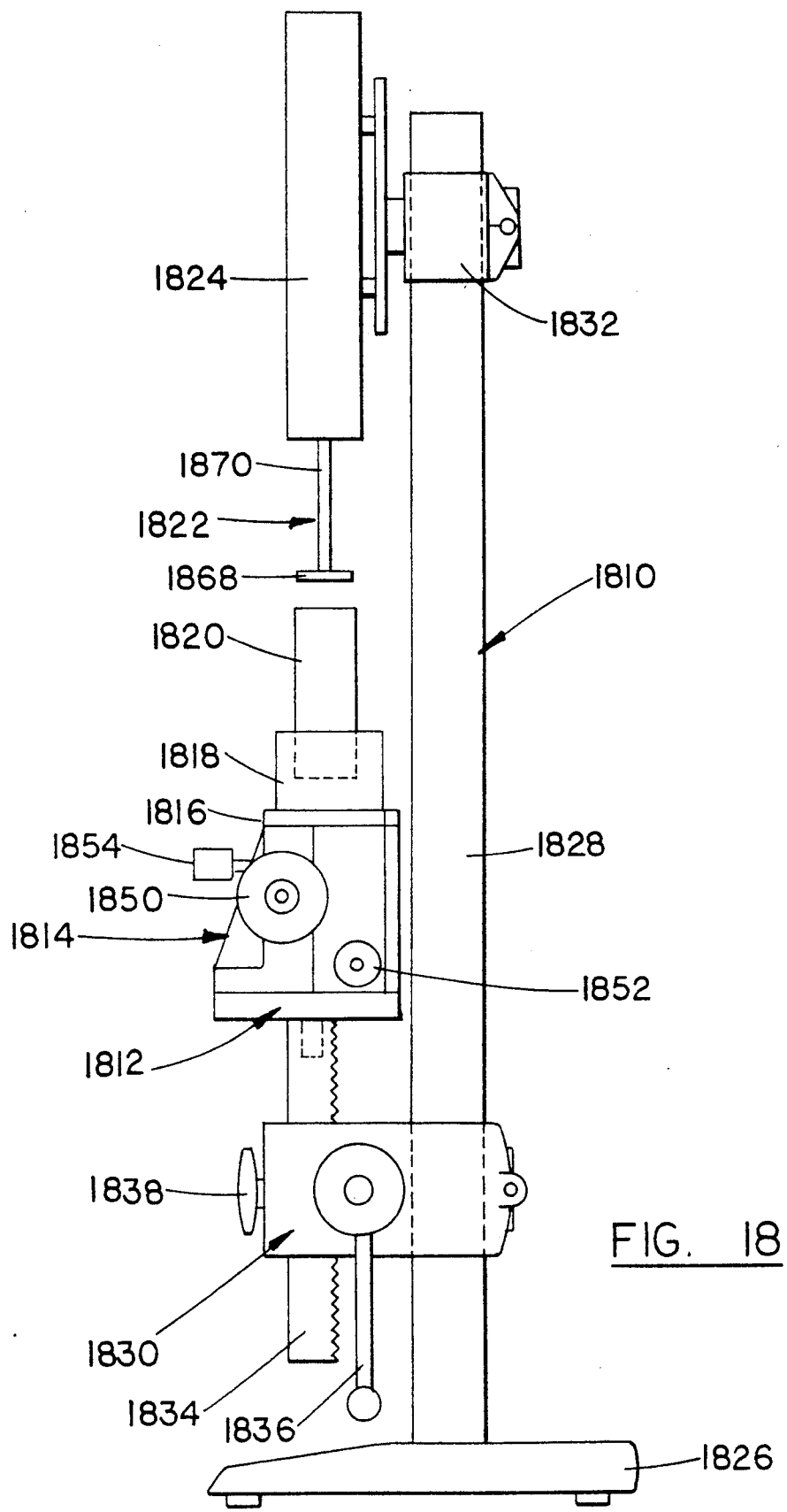
FIG. 18 is a side view of an apparatus used to measure the gel expansion pressure of particulate, absorbent, polymeric compositions.

A side view of the apparatus used to measure gel expansion pressure of the polymeric compositions of the present invention is shown in FIG. 18. The apparatus generally comprises a test stand 1810, a stage mounting platform 1812, a stage 1814, a sample alignment bracket 1816, a sample holder 1818, an absorption cell 1820, a compression foot 1822, and a force gauge 1824.

The test stand 1810 comprises a base 1826, a column 1828 secured to the base 1826, a moveable test platform 1830 secured to the column 1828, and a gauge mounting bracket 1832 secured to the column 1828 above the test platform 1830. The test platform 1830 is operated by a rack and pinion lever system. As shown in FIG. 18, the rack and pinion lever system is shown to comprise a rack 1834, a lever 1836, and a locking screw 1838. The test stand comprises an Ametek Model "RP" test stand #ML-3656 as obtainable from Crown Tool & Supply Co. of Solon, Ohio.

Figure 18A:
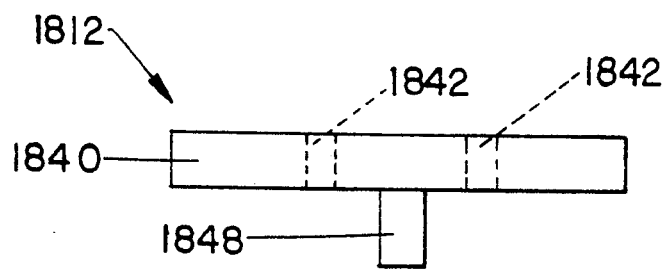
FIG. 18a is a side view of the stage mounting platform of the apparatus of FIG. 18.
Figure 18B:
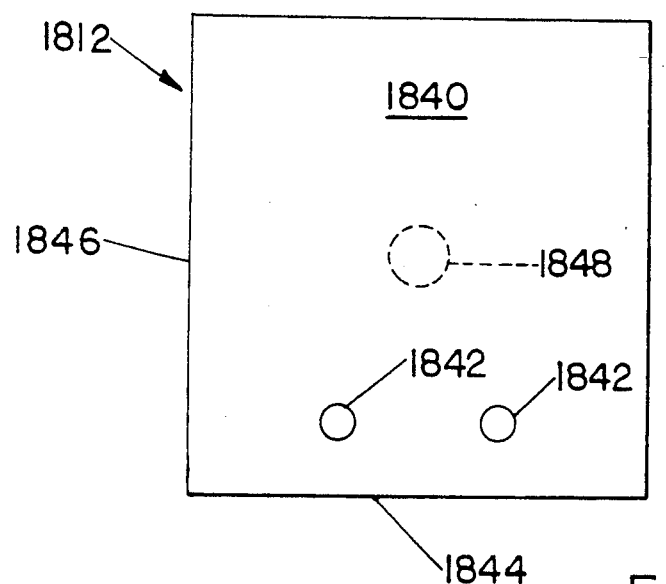
FIG. 18b is a top view of the stage mounting platform of the apparatus of FIG. 18.

The stage mounting platform 1812 is shown is FIGS. 18a and 18b to comprise a 3 inch by 3 inch plate 1840 having two screw holes 1842 drilled in the plate 7/16 inch from a first edge 1844 of the plate 1840 with their centers spaced one inch from opposite second sides 1846 of the plate 1840. A support rod 1848 that is ½ inch long and ¼ inch in diameter is secured to the bottom of the plate 1840. The stage mounting platform 1812 is made from aluminum.

The stage 1814 is secured to the stage mounting platform 1812 by screws through the screw holes 1842. The stage 1814 provides microscope-type motion controls. The stage 1814 is thus provided with a coarse adjustment 1850, a fine adjustment 1852, and a set screw 1854. The stage 1814 comprises a Precision Platform Stage Movement #J3608 as obtainable from Edmund Scientific Co. of Barrington, N.J.

Figure 18C:
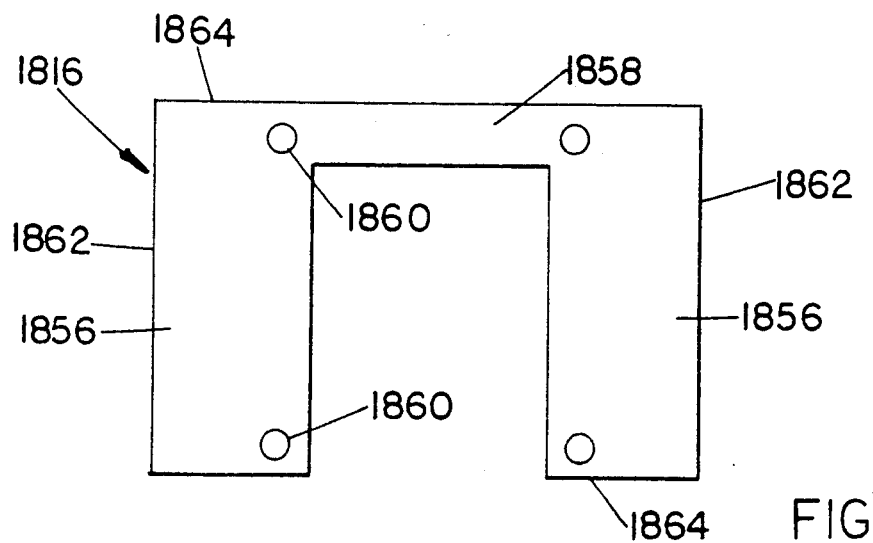
FIG. 18c is a top view of the sample alignment bracket of the apparatus of FIG. 18.

The sample alignment bracket 1816 is shown in FIG. 18c to comprise a U-shaped member formed from a rectangular member approximately 90 mm by 60 mm. The legs 1856 of the "U" are each approximately 25 mm by 60 mm with the base 1858 being approximately 40 mm by 10 mm such that the opening in the "U" is approximately 40 mm by 50 mm. Four 3.5 mm diameter screw holes 1860 are drilled in the sample alignment bracket 20 mm from the side edges 1862 and 5 mm from the end edges 1864. The sample alignment bracket 1816 is made from ¼ inch LEXAN material. The sample alignment bracket 1816 is secured to the top of the stage 1814 through the screw holes by screws.

Figure 18D:
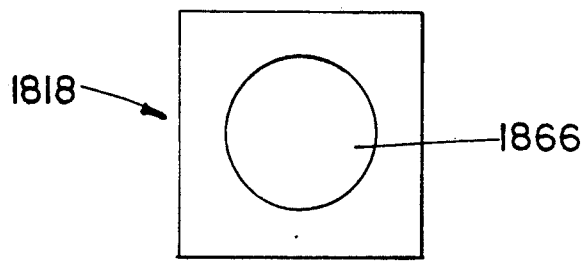
FIG. 18d is a top view of the sample holder of the apparatus of FIG. 18.
Figure 18E:
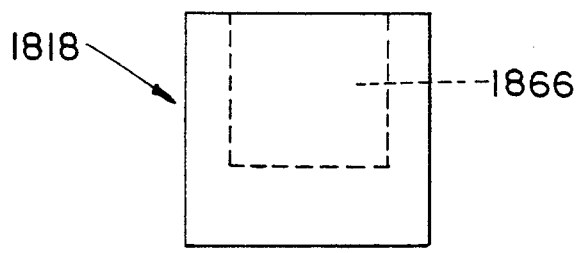
FIG. 18e is a side view of the sample holder of the apparatus of FIG. 18.

The sample holder 1818 is releasably held by the sample alignment bracket 1816 in the opening in the "U". The sample holder 1818 is shown in FIGS. 18d and 18e. The sample holder 1818 is formed from a block about 40 mm wide by 40 mm long by 38 mm high. A center cylindrical opening 1866 having a 25 mm diameter and a 25 mm length is formed in the sample holder 1818. The sample holder is formed from LEXAN.

The absorption cell 1820 is releasably mounted in the sample holder 1818 by placing the absorption cell 1820 in the center cylindrical opening 1866. The absorption cell 1820 should have an inside diameter of 23 mm. The absorption cell 1820 comprises a Standard Absorption Cell #07-102 available from Fisher Scientific of Pittsburgh, Pa.

The force gauge 1824 is secured to the gauge mounting bracket 1832 of the test stand 1810. The force gauge 1824 is an Accuforce Cadet 0-500 g Gauge AFC-1 inverted readout, RS 232 #ML-5801-4 as obtainable from Crown Tool & Supply Co. of Solon, Ohio.

Figure 18F:
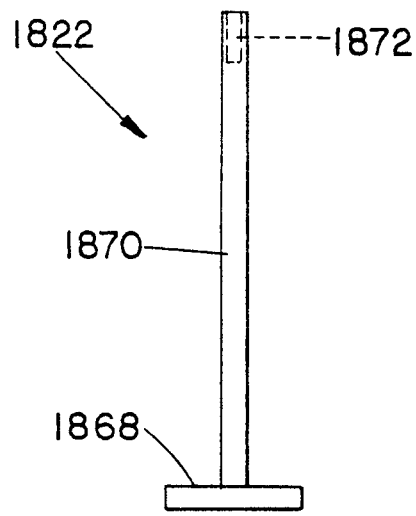
FIG. 18f is a side view of the compression foot of the apparatus of FIG. 18.
Figure 18G:
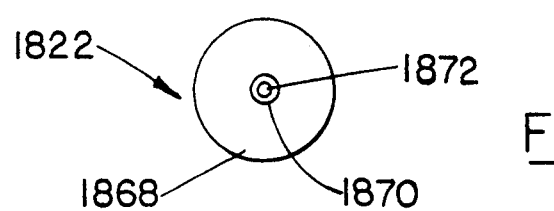
FIG. 18g is a top view of the compression foot of the apparatus of FIG. 18.

A compression foot 1822 as shown in FIGS. 18f and 18g is secured to the force gauge 1824. The compression foot 1832 comprises a foot base 1868 and a stem 1870. The foot base 1868 is formed from a circular plate having a 20.5 mm diameter and a 2.5 mm thickness. The stem 1870 is a rod having a 6.5 mm diameter and being approximately 80 mm long. A gauge attachment bore 1872 approximately ½ inch long and having a 10-32 inside thread is placed in the end of the stem 1870 opposite of the foot base 1868 to secure the compression foot 1822 to the force gauge 1824. The compression foot 1822 is made of aluminum.

An illuminator (not shown) may also be used with the test stand. The illuminator comprises a Fiber Optic Illuminator #N-09745-00 obtainable from Cole-Parmer of Chicago, Ill.

The following procedure is conducted under standard laboratory conditions at 25° C. (73° F.) and 50% relative humidity. Using a standard three decimal place balance, 0.358 grams plus or minus 0.001 grams of a 20/50 cut sample of the polymeric composition is weighed out and placed in the absorption cell 1820. 10.0 ml of Synthetic Urine (a 28× load) is added to the sample. The absorption cell 1820 is placed in the sample holder 1818 which is placed into the sample alignment bracket 1816 on the test stand 1810. The illuminator is turned on. Using the lever 1836 on the test platform 1830 of the test stand 1810, the sample is raised up until the compression foot 1822 is almost touching the fluid. Using the coarse/fine adjustments 1850 and 1852 on the stage 1814, the sample is raised until the level of the fluid is even with the top of the foot base 1868 of the compression foot 1822. This is achieved by sighting across the top of the foot base 1868. The fluid that is on the wall of the absorption cell due to the surface tension will appear as a white band. As the sample is raised, this band moves closer to the foot base 1868, and it will eventually block the silver color of the foot base 1868. When the white band is above the top of the foot base 1868, a silver band will appear. At this point the sample is lowered until the silver band just disappears. When the gel mass reaches the foot base 868, a timer is set for 30 minutes and started. The timer is a Desktop Dual Timer #N-08610-14 obtainable from Cole-Palmer of Chicago, Ill. After 30 minutes, the force in grams is recorded from the force gauge 1824. (The peak force may also be recorded.) The gel expansion pressure (gep) in dynes per square centimeter is calculated as follows: gep=(the force at 30 minutes in grams) multiplied by (981 dynes per gram) and dividing the result by (3.14 square centimeters wherein 3.14 square centimeters is the area of the foot base 1868). The procedure is repeated for two additional samples. The Gel Expansion Pressure of the polymeric composition is the average of three values of the gep as obtained above.

It should be noted that the Gel Expansion Pressure of polymeric compositions under various loadings (not just 28× loadings) can be determined by varying the amount of Synthetic Urine added to the 20/50 cut sample. For example, a "15×" Gel Expansion Pressure may be calculated by adding 5.36 ml of Synthetic Urine to a 0.358 gram sample.

D. Absorptive Capacity

The polymeric composition is placed within a "tea bag", immersed in an excess of Synthetic Urine for a specified period of time, and then centrifuged for a specific period of time. The ratio of polymeric composition final weight after centrifuging minus initial weight (net fluid gain) to initial weight determines the Absorptive Capacity.

The following procedure is conducted under standard laboratory conditions at 23° C. (73° F.) and 50% relative humidity. Using a 6 cm ×12 cm cutting die, the tea bag material is cut, folded in half lengthwise and sealed along two sides with a T-bar sealer to produce a 6 cm ×6 cm tea bag square. The tea bag material utilized is a grade 1234 heat sealable material, obtainable from C. H. Dexter, Division of the Dexter Corp., Windsor Locks, Conn., U.S.A., or equivalent. Lower porosity tea bag material should be used if required to retain fine particles. 0.200 grams plus or minus 0.005 grams of the polymeric composition is weighed onto a weighing paper and transferred into the tea bag, and the top (open end) of the tea bag is sealed. An empty tea bag is sealed at the top and is used as a blank. Approximately 300 milliliters of Synthetic Urine are poured into a 1,000 milliliter beaker. The blank tea bag is submerged in the Synthetic Urine. The tea bag containing the polymeric composition (the sample tea bag) is held horizontally to distribute the material evenly throughout the tea bag. The tea bag is laid on the surface of the Synthetic Urine. The tea bag is allowed to wet, for a period of no more than one minute, and then is fully submerged and soaked for 60 minutes. Approximately 2 minutes after the first sample is submerged, a second set of tea bags, prepared identically to the first set of blank and sample tea bags, is submerged and soaked for 60 minutes in the same manner as the first set. After the prescribed soak time is elapsed, for each set of tea bag samples, the tea bags are promptly removed (using tongs) from the Synthetic Urine. The samples are then centrifuged as described below. The centrifuge used is a Delux Dynac II Centrifuge, Fisher Model No. 05-100-26, obtainable from Fisher Scientific Co. of Pittsburgh, Pa., or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, a 7.935 inch (20.155 cm) inside diameter, and 9 rows each of approximately 106 3/32 inch (0.238 cm) diameter circular holes equally spaced around the circumference of the outer wall, and having a basket floor with six ¼ inch (0.635) cm) diameter circular drainage holes equally spaced around the circumference of the basket floor at a distance of ½ inch (1.27 cm) from the interior surface of the outer wall to the center of the drainage holes, or an equivalent. The basket is mounted in the centrifuge so as to rotate, as well as brake, in unison with the centrifuge. The sample tea bags are positioned in the centrifuge basket with a folded end of the tea bag in the direction of the centrifuge spin to absorb the initial force. The blank tea bags are placed to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm. Once the centrifuge has been stabilized at 1,500 rpm, a timer is set for 3 minutes. After 3 minutes, the centrifuge is turned off and the brake is applied. The first sample tea bag and the first blank tea bag are removed and weighed separately. The procedure is repeated for the second sample tea bag and the second blank tea bag.

The absorptive capacity (ac) for each of the samples is calculated as follows: ac = (sample tea bag weight after centrifuge minus blank tea bag weight after centrifuge minus dry polymeric composition weight) divided by (dry polymeric composition weight). The Absorptive Capacity value for use herein is the average absorptive capacity of the two samples.

E. BET Surface Area Per Unit Mass Measurement

The specific surface area per unit mass (m²/g) of the polymeric composition is determined using the Brunauer-Emmet-Teller (BET) gas adsorption method. This method involves adsorbing a monolayer of a gas (Krypton) on a known mass of the polymeric composition sample at liquid nitrogen temperatures. The adsorbed Krypton is then desorbed by raising the temperature of the sample (thermal desorption) and detected by a thermal conductivity detector (TCD) whose output is connected to an integrating recorder. The peak area of the desorbed Krypton is thus known. Replicate desorption peaks are recorded for each sample. After the sample analysis, the instrument response is determined by preparing a calibration curve. Known amounts of Nitrogen gas (99.99%+) are injected into the system and the instrument response is recorded via the integrating recorder. Linear regression analysis of the instrument response (peak area) versus the amount of sample injected yields a calibration curve. This information is then used to determine the specific area of the various samples using the single-point BET calculation.

The specific equipment used for these analyses is obtainable from the Quantachrome Corporation (Syosset, N.Y.) and consists of the Quantector Outgassing Station and the Quantasorb Sample Analysis Unit. These units are used as described in their respective operating manuals which are incorporated herein by reference. The adsorbate gas mixture used is 0.10% Krypton in Helium. (This gas mixture is obtainable from Alphagaz and is certified as to its concentration such that the gas is used without further analysis.)

3.0 grams plus or minus 0.01 grams is weighed into a glass vial of the apparatus. The glass vial containing the sample is then placed into the gas flow of the instrument. The samples are outgassed for a minimum of 4 hours @30 ml/min Helium flow using the Quantector. After outgassing, the gas flow is changed to 0.10% Krypton in Helium. The glass vial is immersed in liquid Nitrogen and allowed to reach equilibrium. An adsorption curve is generated. The adsorbed Krypton is then desorbed by removing the liquid Nitrogen and immersing the glass vial in warm tap water. The adsorbed Krypton generates a desorption curve and a peak value. Replicate adsorption/desorption measurements are performed on each sample. The total surface area of the sample, $S_t$, is calculated as follows:

$$S_t = (1 - P/P_o)(A/A_c)V_c(NA_{cs}P_a)/RT)$$

wherein P equals the partial pressure of the absorbate; $P_o$ equals the saturated pressure of the absorbate (2.63 mm $H_g$ for Krypton); A equals the signal area; Ac equals the calibration area; $V_c$ equals the calibration volume (cc); N equals Avogadro's number of $6.02 \times 10^{23}$; $A_{cs}$ equals the cross sectional area of absorbate molecule in square meters which is $20.5 \times 10^{-20}$ m² for Krypton; $P_a$ equals ambient pressure (atm); R equals the Gas Constant of 82.1 cc atm/K° mol; and T equals the temperature of the calibration volume (ambient in K°). To convert the calibration volume of Nitrogen to Krypton, the relationship $V_{Kr} = 0.762 V_{N2}$ is used. By constructing a calibration plot of instrument response (peak area) versus the volume injected, $V_c$ can be determined and $A = A_c$. At 25° C., 1 atmosphere pressure (ambient laboratory conditions using 0.10% Krypton in Helium, the relationship for surface area becomes:

$$S_t(m^2) = ((A - C)/B) \times 2.7343$$

wherein A equals the area of the desorbed sample peak; B equals the slope of the calibration curve; and C equals the y intercept of the calibration curve. This total surface area value is then divided by the mass of the sample to obtain a surface area to mass value. The Surface Area to Mass value for use herein is the average of the surface area to mass values for the two replicate samples. (The specifics of the single-point BET calibration are covered in the instrument manuals which are incorporated herein by reference.)

F. Aggregate Percent Method

The percentage of aggregate particles in a polymeric composition sample can be determined by using light microscopy techniques at low magnification (10× to 60×). A particle is considered to be an aggregate if it appears to be made up of more than one precursor particle. By carefully scrutinizing individual particles, the observer can distinguish aggregates from simple nonaggregate particles. Aggregate particles have been found to typically possess many jagged edges and many multiple faces when viewed under the light microscope while simple nonaggregate particles are typically smooth and featureless. Further, due to light scattering around the particles, aggregate particles appear more opaque while simple nonaggregate particles typically appear translucent unless their surfaces are severely scratched or nicked.

A 20/50 cut sample of the polymeric composition is analyzed under the light microscope. The light microscope used is a Stereoscopic Light Microscope Model SMZ-2T as obtainable from Nikon of Garden City, N.J. After mounting a field-finder microscope slide onto the stage of the microscope, about 300 particles of the 20/50 cut sample are placed onto the slide. While illuminating the particles with an illuminator, at least about 50 individual particles are observed at a magnification of 10× to 60×. The illuminator used is a Fiber Optic Illuminator obtainable from the Bausch & Lomb Company of Rochester, N.Y. If a particle is clearly made up of smaller individual particles attached to one another, this particle is recorded as an aggregate. If it is unclear whether or not the particle is made up of more than one particle or the particle is clearly only a single particle, then the particle is recorded as a simple nonaggregate particle. After scrutinizing at least 50 particles, the total number of aggregates is divided by the total number of particles counted and multiplied by 100% to provide a number percent aggregation value for a given sample. On a weight percent basis, the total number of aggregates are separately weighed on a standard scale and the weight of the aggregates is divided by the total weight of the particles counted and multiplied by 100 to provide a weight percent aggregation value for a given sample.

G. Fluid Stability

The objective of this method is to determine the stability of an individual aggregate particle upon exposure to Synthetic Urine.

About 300 particles of a 20/50 cut sample are poured onto a standard 1" by 3" plastic microscope slide. The slide is obtainable from Fisher Scientific Co. of Pittsburgh, Pa. The particles are analyzed under the light microscope. The light microscope used is a Stereoscopic Light Microscope Model SMZ-2T as obtainable from Nikon of Garden City, N.J. The particles are illuminated. The illuminator used is a Fiber Optic Illuminator obtainable from Bausch and Lomb of Rochester, N.Y. The particles are scrutinized at a magnification of $10\times$ to $60\times$. Three relatively large particles with exceptional aggregate characteristics (i.e., comprising a multiplicity of precursor particles) are placed onto separate microscope slides. One of the slides containing a single aggregate particle is placed on the stage of the light microscope. 3 drops of Synthetic Urine are added to the side of and about 2 mm above the aggregate particle. The swelling of the aggregate particle is observed for three minutes. (If necessary, the microscope may be continually refocused so that the aggregate particle or any separated particles are in focus.) During the observation of the swelling aggregate particle, the aggregate particle is observed for small particles breaking off from the main aggregate particle, platelet-like particles floating away from the main aggregate particle, particle expansion only in the two dimensional x-y plane with particles breaking and floating away from the main aggregate particle, or individual particles settling out at the slide/water interface. A particle is considered unstable if the aggregate particle has a large number of broken away component precursor particles. After five minutes, a dissecting needle is used to probe around the particle. The dissecting needle is a Birch handled probe pointer as available from Fisher Scientific of Pittsburgh, Pa. The main aggregate particle (if it still exists) is carefully moved with the dissecting needle to determine whether particles have separated from the main aggregate particle. The dissecting needle may also be carefully "probed" into the main aggregate particle to determine whether the main aggregate particle will remain intact. If the main aggregate particle breaks apart upon gentle probing or there are a number of particles broken off, the particle is considered unstable. After probing the particle, an additional two drops of Synthetic Urine are added from a height of around 1 cm directly above the swollen main aggregate particle. The main aggregate particle is observed for any additional instability of the main aggregate particle. If the instability is excessive, the particle is considered unstable. If the aggregate particle remains relatively stable after each test procedure, the aggregate particle is considered stable. The test is repeated for the remaining two aggregate particles.

H. Particle Size and Mass Average Particle Size

The particle size distribution on a weight percent basis of a 10 gram bulk sample of polymeric composition is determined by sieving the sample through a set of 19 sieves ranging in size from a standard #20 sieve (850 microns) through a standard #400 sieve (38 microns). The sieves are standard sieves as obtainable from the Gilson Company, Inc. of Worthington, Ohio. The procedure is carried out on three stacks of sieves at a time since the equipment used cannot hold all 19 sieves at one time. A first stack contains sieves #20, 25, 30, 35, 40, 45, and 50 plus the sieve pan; the second stack contains sieves #60, 70, 80, 100, 120, and 140 plus the sieve pan; the third stack contains sieves #170, 200, 230, 270, 325, and 400 plus the sieve pan. The particles remaining on each of these sieves are then weighed to determined the particle size distribution on a weight percent basis.

The first stack of sieves is mounted on a shaker and 10.0 grams plus or minus 0.01 grams of a representative bulk sample is placed on the #20 sieve. The shaker used is a Vibratory 3-inch Sieve Shaker Model SS-5 as obtainable from the Gilson Company, Inc. of Worthington, Ohio. The stack is shaken for 3 minutes at approximately 2100 vibrations per minute ("6" on the instrument dial). The sieve pan is then removed and the stack set aside for later weighing. Using a soft brush, the sample remaining on the sieve pan is transferred onto a weighing paper. The second stack of sieves is mounted on the shaker and the sample on the weighing paper is transferred onto the #60 sieve. The second stack is shaken for 3 minutes at approximately 2100 vibrations per minute, the sample remaining on the sieve pan being transferred to a weighing paper and the stack set aside. The third stack of sieves is mounted on the shaker and the sample on the weighing paper is transferred onto the #170 sieve. The third stack is shaken for 3 minutes at approximately 2100 vibrations per minute. A soft brush is used to transfer the contents of each given sieve onto a tared weighing paper. The sample is weighed on a standard three decimal place balance and the weight of the sample on the specific sieve is recorded. This step is repeated, using a fresh weighing paper for each sample, for each sieve, and for the sample remaining on the sieve pan after the third stack of sieves has been shaken. The method is repeated for two additional 10 gram samples. The average of the weights of the three samples for each sieve determine the average particle size distribution on a weight percent basis for each sieve size.

The Mass Average Particle Size of the 10 gram bulk sample is calculated as follows:

$$\text{maps} = \frac{\Sigma (D_i \times M_i)}{\Sigma M_i}$$

wherein maps is the mass average particle size; $M_i$ is the weight of the particles on the specific sieve; and $D_i$ is the "size parameter" for the specific sieve. The size parameter, $D_i$ of a sieve is defined to mean the size (in microns) of the next highest sieve. For example, a standard #50 sieve has a size parameter of 355 microns, which corresponds to the size of the openings in a standard #45 sieve (the next highest sieve). The Mass Average Particle Size for use herein is the average of the mass average particle size of the three samples.

COMPARATIVE EXAMPLE 1

A jacketed 10 liter twin arm stainless steel kneader measuring 220 mm $\times$ 240 mm in the opening and 240 mm in depth, and having two Sigma type blades possessing a rotational diameter of 120 mm is sealed with a lid. An aqueous monomer solution is prepared consisting of 37 weight % monomer. The monomer consists of 75 mole % sodium acrylate and 25 mole % acrylic acid. 5500 grams of the aqueous monomer solution is charged to the kneader vessel, which is subsequently purged with nitrogen gas to remove the remaining entrapped air. Then, the two Sigma type blades are set rotating at rates of 46 rpm and the jacket is heated by the passage of 35° C. water. 2.8 g of sodium persulfate and 0.14 g of L-ascorbic acid are added as polymerization initiators. Polymerization begins about four minutes after the addition of the initiators. A peak temperature of 82° C. is reached inside the reaction system 15 minutes after the addition of the initiators. The hydrated gel polymer is divided into particles about 5 mm in size as the stirring is continued. The lid is removed from the kneader 60 minutes after the start of the polymerization and the material is removed from the kneader.

The resultant hydrated aqueous gel polymer thus obtained is spread on a standard #50 size metal gauze and dried with hot air at 150° C. for 90 minutes. The dried particles are pulverized with a hammer type crusher and sifted with a standard #20 sieve (850 microns) to obtain particles that pass through the standard #20 sieve. The mass average particle size of these particles is 405 microns.

EXAMPLE 1

A solution is prepared consisting of 24.0 grams of methanol and 6.0 grams of glycerol. This solution is applied to and mixed in a standard beaker with 300 grams of precursor particles made in accordance with Comparative Example 1. The particle size distribution of the precursor particles is that 75% by weight passes through a standard #100 sieve (150 microns) and is retained on a standard #170 sieve (90 microns); and 25% by weight passes through a standard #170 sieve (90 microns). The mass average particle size of the precursor particles is 84 microns. This mixture is stirred until all of the precursor particles are wetted by the solution (approximately 1 minute). The resultant mixture is then spread loosely onto a PYREX dish and allowed to stand unheated for 5 minutes to allow the precursor particles to physically associate. The mixture is then heated in a forced air circulation oven at 200° C. for 45 minutes. The resultant particles are then allowed to cool to room temperature. The resultant particles are pushed through a standard #20 sieve (850 microns) to limit the size of the larger particles.

EXAMPLE 2

A solution is prepared consisting of 18.0 grams of isopropanol, 12.0 grams of distilled water, and 6.0 grams of glycerol. This solution is applied to and mixed in a standard beaker with 300 grams of precursor particles made in accordance with Comparative Example 1. The particle size distribution of the precursor particles is that 10% by weight passes through a standard #20 sieve (850 microns) and is retained on a standard #30 sieve (600 microns); 25% by weight passes through a standard #30 sieve (600 microns) and is retained on a standard #40 sieve (425 microns); 25% by weight passes through a standard #40 sieve (425 microns) and is retained on a standard #50 sieve (300 microns); 30% by weight passes through a standard #50 sieve (300 microns) and is retained on a standard #100 sieve (150 microns); and 10% by weight passes through a standard #100 sieve (150 microns). The mass average particle size of the precursor particles is 421 microns. This mixture is stirred until all of the precursor particles are wetted by the solution (approximately 1 minute). The resultant mixture is then spread loosely onto a PYREX dish and allowed to stand unheated for 45 minutes to allow the precursor particles to physically associate. The mixture is then heated in a forced air circulation oven at 200° C. for 45 minutes. The resultant particles are then allowed to cool to room temperature. The resultant particles are pushed through a standard #20 sieve (850 microns) to limit the size of the larger particles.

EXAMPLE 3

A solution is prepared consisting of 18.0 grams of isopropanol, 12.0 grams of distilled water, and 6.0 grams of glycerol. This solution is applied to and mixed in a standard beaker with 300 grams of precursor particles made in accordance with Comparative Example 1. The particle size distribution of the precursor particles is that 50% by weight passes through a standard #40 sieve (425 microns) and is retained on a standard #50 sieve (300 microns); 30% by weight passes through a standard #50 sieve (300 microns) and is retained on a standard #100 sieve (150 microns); and 20% by weight passes through a standard #100 sieve (150 microns). The mass average particle size of the precursor particles is 322 microns. This mixture is stirred until all of the precursor particles are wetted by the solution (approximately 1 minute). The resultant mixture is then spread loosely onto a PYREX dish and allowed to stand unheated for 45 minutes to allow the precursor particles to physically associate. The mixture is then heated in a forced air circulation oven at 200° C. for 45 minutes. The resultant particles are then allowed to cool to room temperature. The resultant particles are pushed through a standard #20 sieve (850 microns) to limit the size of the larger particles.

EXAMPLE 4

A solution is prepared consisting of 18.0 grams of isopropanol, 12.0 grams of distilled water, and 6.0 grams of glycerol. This solution is applied to and mixed in a standard beaker with 300 grams of precursor particles made in accordance with Comparative Example 1. The particle size distribution of the precursor particles is that 60% by weight passes through a standard #50 sieve (300 microns) and is retained on a standard #100 sieve (150 microns); and 40% by weight passes through a standard #100 sieve (150 microns). The mass average particle size of the precursor particles is 205 microns. This mixture is stirred until all of the precursor particles are wetted by the solution (approximately 1 minute). The resultant mixture is then spread loosely onto a PYREX dish and allowed to stand unheated for 10 minutes to allow the precursor particles to physically associate. The mixture is then heated in a forced air circulation oven at 200° C. for 45 minutes. The resultant particles are then allowed to cool to room temperature. The resultant particles are pushed through a standard #20 sieve (850 microns) to limit the size of the larger particles.

EXAMPLE 5

A solution is prepared consisting of 18.0 grams of isopropanol, 12.0 grams of distilled water, and 6.0 grams of glycerol. This solution is applied to and mixed in a standard beaker with 300 grams of precursor particles made in accordance with Comparative Example 1. The particle size distribution of the precursor particles is that 60% by weight passes through a standard #50 sieve (300 microns) and is retained on a standard #100 sieve (150 microns); and 40% by weight passes through a standard #100 sieve (150 microns). The mass average particle size of the precursor particles is 205 microns. This mixture is stirred until all of the precursor particles are wetted by the solution (approximately 1 minute). The resultant mixture is then spread loosely onto a PYREX dish and allowed to stand unheated for 10 minutes to allow the precursor particles to physically associate. The mixture is then heated in a forced air circulation oven at 180° C. for 45 minutes. The resultant particles are then allowed to cool to room temperature. The resultant particles are pushed through a standard #20 sieve (850 microns) to limit the size of the larger particles.

EXAMPLE 6

In a mixer apparatus, 100 parts of a bulk sample of the precursor particles produced in accordance with Comparative Example 1 are thoroughly mixed with a solution containing 2 parts by weight of glycerol and 4 parts by weight of water per 100 parts by weight of the precursor particles. The mass average particle size of the precursor particles is 405 microns. 700 g of the resultant mixture is charged into a bowl dipped in an oil bath (220° C.) and is heated for 80 minutes while being gently stirred. The resultant particles are pushed through a standard #18 wire gauze (1000 microns).

COMPARATIVE EXAMPLE 2

In a mixer apparatus, 100 parts of the precursor particles produced in accordance with Comparative Example 1 is mixed with a solution containing 0.5 parts by weight of glycerol, 2 parts by weight of water and 0.5 parts by weight of isopropanol per 100 parts by weight of the precursor particles. The mass average particle size of the precursor particles is 405 microns. The resultant mixture is heated in a continuous drier. The average residence time in the drier is about 50 minutes, and the temperature of the material at the outlet of the drier is approximately 190° C. The resultant particle are pushed through a standard #20 wire gauze (850 microns). The resultant particles have the following particle size distribution: 0% retained on a #20 sieve; 0% retained on a #25 sieve; 0% retained on a #30 sieve; 0% retained on a #35 sieve; 0.3% retained on a #40 sieve; 1.1% retained on a #45 sieve; 2.2% retained on a #50 sieve; 4.4% retained on a #60 sieve; 9.4% retained on a #70 sieve; 10.9% retained on a #80 sieve; 10.4% retained on a #100 sieve; 10.9% retained on a #120 sieve; 12.6% retained on a #140 sieve; 5.4% retained on a #170 sieve; 7.2% retained on a #200 sieve; 6.3% retained on a #230 sieve; 6.0% retained on a #270 sieve; 3.5% retained on a #325 sieve; 3.3% retained on a #400 sieve; and 4.7% retained on the sieve pan. The mass average particle size of the particles is 465 microns.

EXAMPLE 7

A jacketed 10 liter twin arm stainless steel kneader measuring 220 mm ×240 mm in the opening and 240 mm in depth, and having two Sigma type blades possessing a rotational diameter of 120 mm, is sealed with a lid. An aqueous solution is prepared consisting of 37 weight % monomer. The monomer consists of 75 mole % sodium acrylate and 25 mole % acrylic acid. 5500 grams of the aqueous monomer solution is charged to the kneader vessel, which is subsequently purged with nitrogen gas to remove the remaining entrapped air. Then, the two Sigma type blades are set rotating at rates of 46 rpm and the jacket is heated by the passage of 35° C. water. 2.8 g of sodium persulfate and 0.14 g of L-ascorbic acid are added as polymerization initiators. Polymerization begins about four minutes after the addition of the initiators. A peak temperature of 82° C. is reached inside the reaction system 15 minutes after the addition of the initiators. The hydrated gel polymer is divided into particles about 5 mm in size as the stirring is continued. The lid is removed from the kneader 60 minutes after the start of the polymerization and the material is removed from the kneader.

The resultant hydrated aqueous gel polymer thus obtained are spread on a standard #50 metal gauze (300 microns) and dried with hot air at 150° C. for 90 minutes. The dried particles are pulverized (stronger than in the case of the particles produced in Comparative Example 1) with a hammer type crusher and sifted with a standard #20 wire gauze (850 microns) to obtain particles that pass through a standard #20 sieve (850 microns). The mass average particle size of these precursor particles is 153 microns.

In a mixer apparatus, 100 parts of the precursor particles produced in accordance with the above procedure are mixed with a solution containing 4 parts by weight of glycerol, 8 parts by weight of water and 2 parts by weight of isopropanol per 100 parts by weight of the precursor particles. 500 g of the resultant mixture is charged into a bowl dipped in an oil bath (210° C.) and is subjected to heat-treatment for 95 minutes while being gently stirred. The resultant particles are pushed through a standard #18 metal gauze (1000 microns).

COMPARATIVE EXAMPLE 3

A jacketed 10 liter twin arm stainless steel kneader measuring 220 mm ×240 mm in the opening and 240 mm in depth, and having two Sigma type blades possessing a rotational diameter of 120 mm, is sealed with a lid. An aqueous solution is prepared consisting of 37 weight % monomer. The monomer consists of 75 mole % sodium acrylate and 25 mole % acrylic acid. 5500 grams of the aqueous monomer solution is charged to the kneader vessel, which is subsequently purged with nitrogen gas to remove the remaining entrapped air. Then, the two Sigma type blades are set rotating at rates of 46 rpm and, at the same time, the jacket is heated by the passage of 35° C. water. 2.8 g of sodium persulfate and 0.14 g of L-ascorbic acid are added as polymerization initiators. Polymerization begins about four minutes after the addition of the initiators. A peak temperature of 82° C. is reached inside the reaction system 15 minutes after the addition of the initiators. The hydrated gel polymer is divided into particles about 5 mm in size as the stirring is continued. The lid is removed from the kneader 60 minutes after the start of the polymerization and the material is removed from the kneader. The resultant hydrated particles of aqueous gel polymer thus obtained are spread on a standard #50 wire gauze (300 microns) and dried with hot air at 150° C. for 90 minutes. The dried particles are pulverized (stronger than in the case of the particles produced in Comparative Example 1) with a hammer type crusher and sifted with a standard #20 wire gauze (850 microns) to obtain particles that passes through a standard #20 sieve (850 microns). The mass average particle size of these precursor particles is 319 microns.

In a mixer apparatus, 100 parts of the precursor particles produced in accordance with the above procedure is mixed with a solution containing 0.5 parts by weight of glycerol, 2 parts by weight of water, and 0.5 parts by weight of isopropanol per 100 parts by weight of the precursor particles. The resultant mixture is heated in a continuous drier. The average residence time in the drier is about 50 minutes, and the temperature of the material at the outlet of the drier is approximately 195° C. In a mixer apparatus, 100 parts of the resultant material thus obtained is mixed with 5 parts of water. The mixture is let stand for 30 minutes in an atmosphere of 80° C. to water agglomerate the particles together and is disintegrated (crushed and granulated) to obtain particles that pass through a standard #20 sieve (850 microns).

The results of the various tests on the examples is shown below in Table 1:

TABLE 1

|  | Mass Average Bulk (micron) | Precursor Mass Avg. Bulk (micron) | Mass Avg. Shift | Fluid Stability 20/50 (Y/N) | Absorptive Capacity 20/50 (g/g) | Gel Expansion Pressure 20/50 (kdyn/cm$^2$) | Swelling Rate 20/50 (g/g/sec) | Surface Area 20/50 (m$^2$/g) |
|---|---|---|---|---|---|---|---|---|
| Comp' Ex' 1 | 405 | N/A | N/A | N/A | 46.0 | 9.2 | 0.22 | 0.020 |
| Example 1 | 216 | 84 | 157.0% | Yes | 36.8 | 14.6 | 1.09 | 0.169 |
| Example 2 | 592 | 421 | 40.6% | Yes | 38.5 | 39.2 | 0.36 | 0.033 |
| Example 3 | 501 | 322 | 55.6% | Yes | 36.7 | 39.8 | 0.45 | 0.042 |
| Example 4 | 329 | 205 | 60.5% | Yes | 33.9 | 29.2 | 0.82 | 0.064 |
| Example 5 | 328 | 205 | 60.0% | Yes | 33.5 | 29.8 | 0.97 | 0.065 |
| Example 6 | 537 | 405 | 32.6% | Yes | 35.7 | 38.7 | 0.33 | 0.033 |
| Comp' Ex' 2 | 465 | 405 | 14.8% | Yes | 42.6 | 16.1 | 0.17 | 0.021 |
| Example 7 | 303 | 153 | 98.0% | Yes | 34.9 | 25.9 | 0.98 | 0.067 |
| Comp' Ex' 3 | 398 | 319 | 24.8% | No | 38.7 | 18.2 | 0.21 | 0.037 |

Table 1 shows that the polymeric compositions of the present invention have mass average particle sizes at least about 25% greater than the mass average particle sizes of the precursor particles used to form such polymeric compositions. Particle size shifts of this magnitude and direction are indicative of the formation of large numbers of aggregates and aggregates having large numbers of component precursor particles. Further, Table 1 shows that the aggregates formed in Examples 1-7 are fluid stable, indicating the presence of a large degree of interparticle crosslink bonding in the aggregates. Table I also shows that the polymeric compositions of the present invention, exemplified by Examples 1-7, have greater resistance to compression (i.e., higher gel expansion pressure) and higher swelling rates than their corresponding precursor particles.

Table 1 also shows that Comparative Examples 2 and 3 have smaller particle size shifts versus their precursors than Examples 1-7, indicating the creation of fewer aggregates. Additionally, the aggregates of Comparative Example 3, a water agglomerated sample, demonstrate an overall trend toward fluid instability, meaning that the actual particle size shift due to any interparticle crosslinking is significantly smaller than the 24.8% shift shown in Table 1. Table 1 also shows that the swelling rates of Comparative Examples 2 and 3 are lower than the polymeric compositions of the present invention.

The above properties relate to the performance of polymeric compositions in absorbent products such that the polymeric compositions of the present invention should provide improved performance over the corresponding precursor particles and/or the comparative examples described above when used in absorbent products such as absorbent members or absorbent articles such as diapers.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A particulate, absorbent, polymeric composition comprising interparticle crosslinked aggregates, said interparticle crosslinked aggregates comprising (i) precursor particles of substantially water-insoluble, absorbent, hydrogel-forming, polymer material, and (ii) an interparticle crosslinking agent reacted with said polymer material of said precursor particles to form covalent crosslink bonds between said precursor particles, said interparticle crosslinked aggregates being present in the polymeric composition in an amount such that the polymeric composition has a mass average particle size at least about 25% greater than the mass average particle size of said precursor particles.

2. The polymeric composition of claim 1 having a mass average particle size at least about 30% greater than the mass average particle size of said precursor particles.

3. The polymeric composition of claim 1 having a mass average particle size at least about 50% greater than the mass average particle size of said precursor particles.

4. The polymeric composition of claim 1 wherein at least said interparticle crosslinked aggregates are surface treated.

5. The polymeric composition of claim 4 wherein at least said interparticle crosslinked aggregates are surface crosslinked.

6. The polymeric composition of claim 1 wherein said polymer material of said precursor particles possesses a carboxyl group, and said interparticle crosslinking agent has at least two functional groups per molecule capable of reacting with said carboxyl group.

7. The polymeric composition of claim 1 wherein said interparticle crosslinking agent is mixed with water, an organic solvent, or mixtures thereof.

8. The polymeric composition of claim 1 comprising greater than about 50% by weight of the polymeric composition of said interparticle crosslinked aggregates.

9. A particulate, absorbent, polymeric composition comprising interparticle crosslinked aggregates, said interparticle crosslinked aggregates comprising (i) substantially dry precursor particles of substantially water-insoluble, absorbent, hydrogel-forming, polymer material; said polymer material being selected from the group consisting of hydrolyzed starch-acrylonitrile graft copolymer, partially neutralized starch-acrylonitrile graft copolymer, starch-acrylic acid graft copolymer, partially neutralized starch-acrylic acid graft copolymer, saponified vinyl acetate-acrylic ester copolymers, hydrolyzed acrylonitrile or acrylamide copolymers, slightly network crosslinked products of any of the foregoing copolymers, partially neutralized polyacrylic acid, or slightly network crosslinked products of partially neutralized polyacrylic acid; and (ii) an interparticle crosslinking agent selected from the group consisting of polyhydric alcohol compounds, polyglycidyl ether compounds, polyfunctional aziridine compounds, polyfunctional amine compounds, or polyfunctional isocyanate compounds; said interparticle crosslinking agent being reacted with said polymer material of said precursor particles to form crosslink bonds between said precursor particles; said interparticle crosslinked aggregates being present in the polymeric composition in an amount such that the polymeric composition has a mass average particle size at least about 30% greater than the mass average particle size of said precursor particles.

10. The polymeric composition of claim 9 wherein said interparticle crosslinking agent is mixed with water, a hydrophilic organic solvent, or mixtures thereof.

11. The polymeric composition of claim 10 wherein from about 0.01 to about 30 parts by weight of said interparticle crosslinking agent per 100 parts by weight of said precursor particles is mixed with from about 0.01 to about 20 parts by weight of water per 100 parts by weight of said precursor particles.

12. The polymeric composition of claim 10 wherein from about 0.01 to about 30 parts by weight of said interparticle crosslinking agent per 100 parts by weight of said precursor particles is mixed with from about 0.01 to about 60 parts by weight of a hydrophilic organic solvent per 100 parts by weight of said precursor particles.

13. The polymeric composition of claim 10 wherein from about 0.01 to about 30 parts by weight of said interparticle crosslinking agent per 100 parts by weight of said precursor particles is mixed with from about 0.01 to about 60 parts by weight of a mixture of water and a hydrophilic organic solvent per 100 parts by weight of said precursor particles.

14. The polymeric composition of claim 9 wherein at least said interparticle crosslinked aggregates are surface crosslinked.

15. The polymeric composition of claim 9, 10, 13, or 14 having a mass average particle size at least about 50% greater than the mass average particle size of said precursor particles.

16. The polymeric composition of claim 9 comprising greater than about 50% by weight of the polymeric composition of said interparticle crosslinked aggregates.

17. A particulate, absorbent, polymeric composition comprising interparticle crosslinked aggregates, said interparticle crosslinked aggregates comprising (i) substantially dry precursor particles of substantially water-insoluble, absorbent, hydrogel-forming, polymer material; said polymer material consisting essentially of slightly network crosslinked products of partially neutralized polyacrylic acid; and (ii) an interparticle crosslinking agent selected from the group consisting of glycerol; trimethylol propane; 1,2-propanediol; 1,3-propanediol or ethylene glycol; said interparticle crosslinking agent being reacted with said polymer material of said precursor particles to form crosslink bonds between said precursor particles; said interparticle crosslinked aggregates being present in the polymeric composition in an amount such that the polymeric composition has a mass average particle size at least about 30% greater than %he mass average particle size of said precursor particles.

18. The polymeric composition of claim 17 wherein the mass average particle size of said precursor particles is less than about 600 microns.

19. The polymeric composition of claim 18 wherein said precursor particles are generally spherical in shape.

20. The polymeric composition of claim 18 wherein said precursor particles are generally irregular in shape.

21. The polymeric composition of claim 20 wherein said interparticle crosslinking agent is glycerol.

22. The polymeric composition of claim 21 wherein at least said interparticle crosslinked aggregates are surface crosslinked.

23. The polymeric composition of claim 22 having an Absorptive Capacity greater than about 20 grams of Synthetic Urine per gram of polymeric composition.

24. The polymeric composition of claim 23 having a Gel Expansion Pressure greater than about 20 kilodynes per square centimeter and a Swelling Rate greater than about 0.3 g/g/sec in Synthetic Urine, wherein the Gel Expansion Pressure and Swelling Rate are measured at a load of 28 grams of Synthetic Urine per gram of the polymeric composition.

25. The polymeric composition of claim 17 wherein said interparticle crosslinking agent is mixed with water, a hydrophilic organic solvent, or mixtures thereof.

26. The polymeric composition of claim 25 wherein from about 0.5 to about 10 parts by weight of said interparticle crosslinking agent per 100 parts by weight of said precursor particles is mixed with from about 1 to about 20 parts by weight of water, a hydrophilic organic solvent, or mixtures thereof per 100 parts by weight of said precursor particles.

27. The polymeric composition of claim 26 wherein said interparticle crosslinking agent is glycerol, and said hydrophilic organic solvent is selected from the group consisting of methanol, ethanol, isopropanol, or mixtures thereof.

28. The polymeric composition of claim 27 wherein at least said interparticle crosslinked aggregates are surface crosslinked.

29. The polymeric composition of claim 17, 18, 21, 22, 27, or 28 having a mass average particle size at least about 50% greater than the mass average particle size of said precursor particles.

* * * * *

UNITED STATES PATENT AND TRADEMARK OFFICE
CERTIFICATE OF CORRECTION

PATENT NO. : 5,300,565
DATED : April 5, 1994
INVENTOR(S) : Charles J. Berg et al.

It is certified that error appears in the above-indentified patent and that said Letters Patent is hereby corrected as shown below:

Column 22, line 16 "Re. No." should read --No. Re.--

Column 37, line 29 delete "-"

Column 38, line 39 "154" should read --3/8--

Column 45, line 42 "868" should read --1868--

Column 49, line 50 "l" should read --1--

Column 55, line 40 "l" should read --1--

Column 58, line 13 "%he" should read --the--

Signed and Sealed this

Twenty-ninth Day of August, 1995

Attest:

BRUCE LEHMAN

*Attesting Officer*     *Commissioner of Patents and Trademarks*